US009938585B2

(12) United States Patent
Yamanaka et al.

(10) Patent No.: US 9,938,585 B2
(45) Date of Patent: Apr. 10, 2018

(54) METHOD FOR SCREENING INDUCED PLURIPOTENT STEM CELLS

(71) Applicant: KYOTO UNIVERSITY, Kyoto-shi, Kyoto (JP)

(72) Inventors: Shinya Yamanaka, Kyoto (JP); Kazutoshi Takahashi, Kyoto (JP); Michiyo Koyanagi, Kyoto (JP); Mari Ohnuki, Kyoto (JP)

(73) Assignee: KYOTO UNIVERSITY, Kyoto-shi, Kyoto (JP)

( * ) Notice: Subject to any disclaimer, the term of this patent is extended or adjusted under 35 U.S.C. 154(b) by 0 days.

(21) Appl. No.: 15/600,068

(22) Filed: May 19, 2017

(65) Prior Publication Data

US 2017/0253934 A1    Sep. 7, 2017

Related U.S. Application Data

(62) Division of application No. 14/235,391, filed as application No. PCT/JP2012/004747 on Jul. 25, 2012, now Pat. No. 9,677,141.

(60) Provisional application No. 61/511,156, filed on Jul. 25, 2011.

(51) Int. Cl.
*C12Q 1/68* (2006.01)
*G01N 33/50* (2006.01)

(52) U.S. Cl.
CPC ......... *C12Q 1/6888* (2013.01); *C12Q 1/6881* (2013.01); *G01N 33/5023* (2013.01); *G01N 33/5073* (2013.01); *C12Q 2600/158* (2013.01)

(58) Field of Classification Search
None
See application file for complete search history.

(56) References Cited

U.S. PATENT DOCUMENTS

2001/0051344 A1    12/2001    Shalon et al.
2009/0068742 A1    3/2009    Yamanaka

FOREIGN PATENT DOCUMENTS

| JP | 2010-172225 A | 8/2010 |
| RU | 2340896 C1 | 12/2008 |
| WO | WO 2007/069666 A1 | 6/2007 |
| WO | WO 2008/118820 A2 | 10/2008 |
| WO | WO 2010/137348 A1 | 12/2010 |
| WO | WO 2011/087154 A1 | 7/2011 |

OTHER PUBLICATIONS

Bock et al., "Reference Maps of Human ES and iPS Cell Variation Enable High-Throughput Characterization of Pluripotent Cell Lines," Cell, vol. 144, No. 3, Feb. 4, 2011, pp. 439-452, XP028203109.
Chinese Office Action and Search Report, dated Apr. 28, 2015, for Chinese Application No. 201280036781.9, with partial translation thereof.
International Search Report issued in PCT/JP2012/004747 dated Oct. 30, 2012.
Kim et al., "miR-371-3 Expression Predicts Neural Differentiation Propensity in Human Pluripotent Stem Cells," Cell Stem Cell, vol. 8, No. 6, Jun. 3, 2011, pp. 695-706, XP028386711.
Kowalski et al., "Intergenic Splicing between a HERV-H Endogenous Retrovirus and Two Adjacent Human Genes," Genomics, vol. 57, No. 3, May 1999, pp. 371-379, XP004444907.
Koyanagi-Aoi et al., "Differentiation-defective phenotypes revealed by large-scale analyses of human pluripotent stem cells," Proceedings of the National Academy of Sciences, vol. 110, No. 51, Dec. 17, 2013, pp. 20569-20574, XP055173687.
Miura, K. et al. "Variation in the safety of induced pluripotent stem cell lines," Nature Biotechnology, Aug. 2009, vol. 27, No. 8, pp. 743-745.
Nakagawa, M. et al. "Generation of induced pluripoten stem cells without Myc from mouse and human fibroblasts," Nature Biotechnology, Jan. 2008, vol. 26, No. 1, pp. 101-106.
Partial Supplementary European Search Report for European Application No. 12818307.6, dated Mar. 17, 2015.
Pick, M. et al. "Clone- and Gene-Specific Aberrations of Parental Imprinting in Human Induced Pluripotent Stem Cells," Stem Cells, 2009, vol. 27, Iss. 11, pp. 2686-2690.
Takahashi K. et. al., "Induction of Pluripotent Stem Cells from Mouse Embryonic and Adult Fibroblast Cultures by Defined Factors", Cell, Aug. 25, 2006, vol. 126, pp. 663-676.
Takahashi, K. et al. "Induction of Pluripotent Stem Cells from Adult Human Fibroblasts by Defined Factors," Cell, Nov. 30, 2007, vol. 131, Iss. 5, pp. 861-872.
Tsuneyoshi et al., "PRDM14 suppresses expression of differentiation marker genes in human embryonic stem cells," Biochemical and Biophysical Research and Communications, vol. 367, 2008, pp. 899-905.
Weiss, "The Agilent Gene Expression Platform: LINC-ing To The Future with Increased Density," Agilent Technologies Slide Presentation, Nov. 18, 2010, 16 pages, XP055173756.
Written Opinion of the International Searching Authority issued in PCT/JP2012/004747 dated Oct. 30, 2012.
Yu, J. et al. "Induced Pluripotent Stem Cell Lines Derived from Human Somatic Cells," Science, Dec. 21, 2007, vol. 318, pp. 1917-1920.
Gerrard, Lesley, et al., "Differentiation of Human Embryonic Stem Cells to Neural Lineages in Adherent Culture by Blocking Bone Morphogenetic Protein Signaling" Stem Cells, 2005, 23, 1234-1241, www.StemCells.com.
Kowalski, Paul E., et al., "A Human Endogenous Retrovirus Suppresses Translation of an Associated Fusion Transcript, PLA2L" Journal of Virology, Jul. 1998, vol. 72, No. 7, pp. 6164-6168.
Kroese, Mark, et al., "Genetic tests and their evaluation: Can we answer the key questions?" Genetics in Medicine 6(6), 2004, pp. 475-480.
Lucentini, Jack, "Gene Association Studies Typically Wrong, Reproducible gene-disease associations are few and far between" The Scientist, 18(24):20, 2004, pp. 1-6

*Primary Examiner* — Celine Qian
(74) *Attorney, Agent, or Firm* — Birch, Stewart, Kolasch & Birch, LLP

(57) ABSTRACT

The present invention provides a method for screening for iPS cells exhibiting differentiation resistance using a marker identified as lincRNA or mRNA that is specifically expressed in an iPS cell line exhibiting differentiation resistance, and such markers.

2 Claims, 3 Drawing Sheets

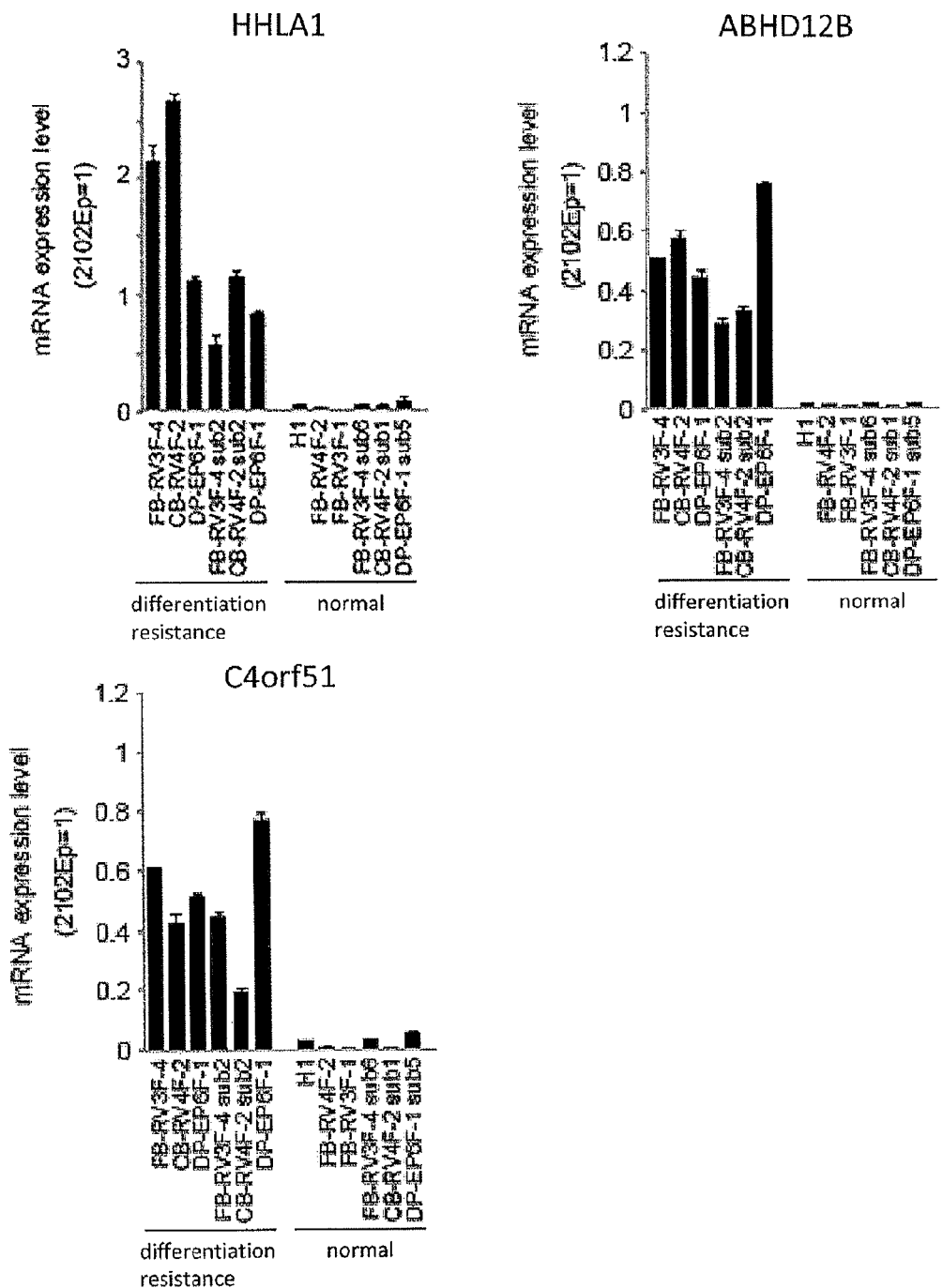
{Fig. 1}

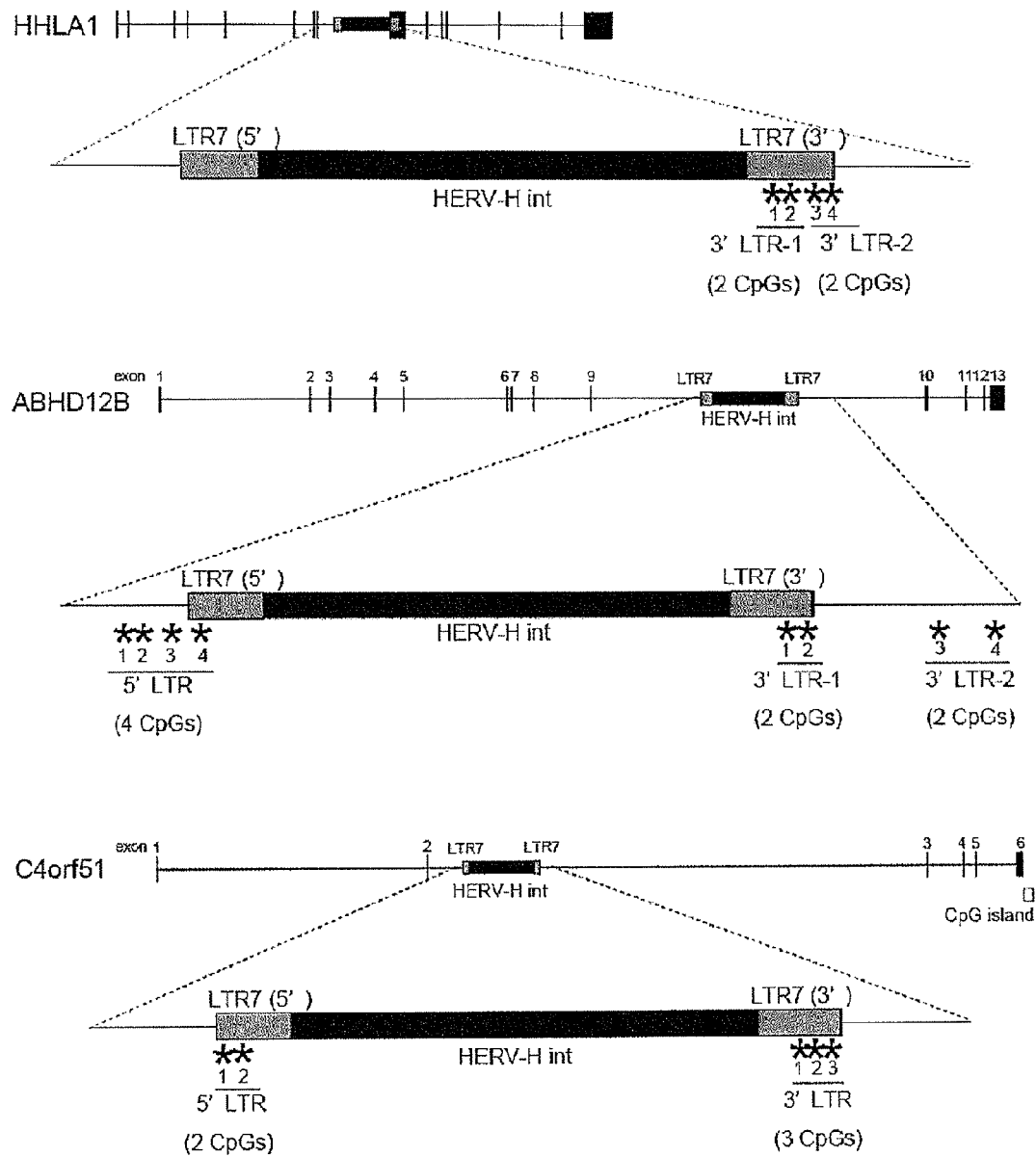
{Fig. 2}

{Fig. 3}
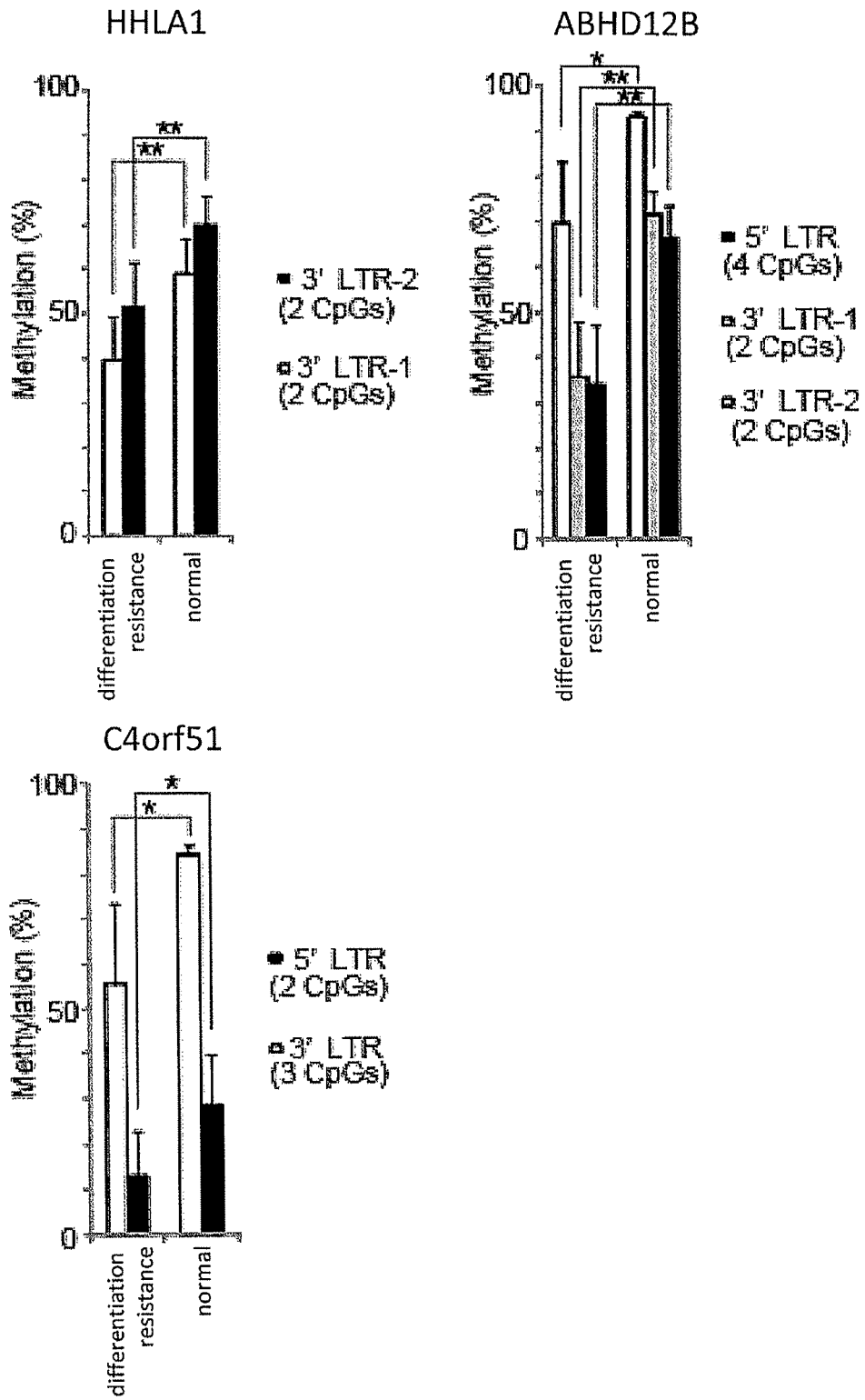

SEQUENCE LISTING

```
<160> NUMBER OF SEQ ID NOS: 40

<210> SEQ ID NO 1
<211> LENGTH: 450
<212> TYPE: DNA
<213> ORGANISM: retroviral virus

<400> SEQUENCE: 1
tgtcaggcct ctgagcccaa gctaagccat cacatcccct gtgactagca catatacgct      60
cagatggcct gaagtaactg aagaatcaca aagaagtgaa aatgccctgc cccacccttaa    120 ctgatgacat tccaccacaa aagaagtgaa aatggccggt ccttgcctta agtgatgaca    180
ttaccttgta agagtccttt tcctggctca tcctagctca aaaatctccc ctactgagca    240
ccctgcgacc cccactccta cccgccaaag aacaacccccc ctttgactgt aattgtcctt   300 tacctacccca aatcctataa aacagcccca cccctatctc cctttgctga ctctcttttc    360
ggactcagcc cgcctgcacc caggtgatta aaagctttat tgctcacaca aagcctgttt    420
ggtggtctct tcacacggac gcgcatgaaa                                       450
```

<210> SEQ ID NO 2
<211> LENGTH: 453
<212> TYPE: DNA
<213> ORGANISM: Homo sapiens

<400> SEQUENCE: 2

```
tgtcaggcct ctgagcccaa gccaagccat cgcaacccct gtgacttgca cctatacgcc        60
cagatggcct gaagtaactg aagaatcaca aaagaagtga atatgccctg ccccacctta       120
actgatgaca ttccaccaca aaagaagtgt aaatggccgg tccttgcctt aactgatgac       180
attaccttgt gaaagtcctc ttcctggctc atcctggctc aaaaagcacc cccactgagc       240
accttgagac ccccactcct gcccgccaga gaacaaaccc cctttgactg taattttcct       300
ttacctaccc aaatcctata aaacggcccc acccttatct cccttcactg actctctttt       360
cggactcagc ccgcctgcac ccaggtgaaa taaacagctt tattgctcac acaaagcctg       420
tttggtggtc tcttcacacg dacgcgcatg aaa                                    453
```

<210> SEQ ID NO 3
<211> LENGTH: 453
<212> TYPE: DNA
<213> ORGANISM: Homo sapiens

<400> SEQUENCE: 3

```
tgtcaggcct ctgagcccaa gccaagccat cgcaacccct gtgacttgca cctatacgcc        60
cagatggcct gaagtaactg aagaatcaca aaagaagtga atatgccctg ccccacctta       120
actgatgaca ttccaccaca aaagaagtgt aaatggctgg tccttgcctt aactgatgac       180
attaccttgt gaaagtcctc ttcctggctc atcctggctc aaaaagcacc cccactgagc       240
accttgagac ccccactcct gcccgccaga gaacaaaccc cctttgactg taattttcct       300
ttacctaccc aaatcctata aaacggcccc acccttatct cccttcactg actctctttt       360
cggactcagc ccgcctgcac ccaggtgaaa taaacagctt tattgctcac acaaagcctg       420
tttggtggtc tcttcacacg dacgcacatg aaa                                    453
```

<210> SEQ ID NO 4
<211> LENGTH: 451
<212> TYPE: DNA
<213> ORGANISM: Homo sapiens

<400> SEQUENCE: 4

```
tgtcaggcct ctgagcccaa gccaagccat cgcatcccct gtgacttgca ggtatctgcc        60
cagatggcct gaagtaactg aagaatcaca aaagaagtga atatgccctg ccccacctta       120
actgatgaca ttccaccaca aaagaagtat aaatggccgg tccttgcctt aagtgatgac       180
actaccttgt gaaagtcctt ttcctggctc atcctggctc agaagctccc ccactgagca       240
ccttgtgacc cccaccccctg cccaccagag aacaaccccc tttgactgta attttccatt       300
accttcccaa atcctataaa acagccccac ccctatctcc cttggctgac tctcttttcg       360
gactcagccc acctgcaccc aggtgaaata acagccatg ttgctcacac aaagcctgtt       420
tggtggtctc ttcacacgga cgcgcatgaa a                                      451
```

<210> SEQ ID NO 5
<211> LENGTH: 491
<212> TYPE: DNA
<213> ORGANISM: Homo sapiens

<400> SEQUENCE: 5

```
tgtcaggcct ctgagcccaa gccaagccat cgcatccct gtgacttgca catatacgcc      60
cagatggcct gaagtaactg aagaatcaca aagaagtga aaaggccctg ccctgcctta    120
actgatgaca ttccaccatt gtgatttgtt cctgccccac cttaactgag tgattaaccc    180
tgtgaatttc cttctcctgg ctcagaagct gccccacctt aactgagtga ttaaccctgc    240
gaatttcctt ctcctggctc agaagctccc ccactgagca ccttgtgacc ccgcccctg    300 cccaccagag agcaaccccc tttgactgta attttccatt accttcccaa atcctataaa    360
acggccccac ccctatctcc cttggctgac tctctttgcg gactcagccc gcctgcaccc    420
aggtgaaata acagccatg ttgctcacac aaagcctgtt ggtggtctc ttcacacaga    480 cgcgcatgaa a                                                        491
```

<210> SEQ ID NO 6
<211> LENGTH: 452
<212> TYPE: DNA
<213> ORGANISM: Homo sapiens

<400> SEQUENCE: 6

```
tgtcaggcct ctgagcccaa gccaagccat cgcatccct gtgacttgca catatacgcc      60
cagatggcct gaagtaactg aagaatcaca aagaagtga atatgcccag ccccaccta    120 actgatgaca ttccaccaca aaaagaagtg taaatggccg gtccttgcct taactgatga    180
cattaccttg tgaaagtcct tttcctggct cattctggct caaatagcac ccccattgag    240
caccttgcaa cccccactcc tgcccgccag agaacaaacc cctttgact gtaattttcc    300 tttacccacc caaatcatat aaaatggccc caccttatc tccttcgct gactctcttt    360 tcagactcag cccaccctgca cccaggtgat taaaagcttt attgctcaca caaagcctgt    420
ttggtggtct cttcacacgg atgcgcaaga aa                                 452
```

<210> SEQ ID NO 7
<211> LENGTH: 450
<212> TYPE: DNA
<213> ORGANISM: Homo sapiens

<400> SEQUENCE: 7

```
tgtcaggcct ctgagcccaa gccaagccat cacatccct gtgacttgca catatatgcc      60
cagatggcct gaagtaactg aagaatcaca aagaagtga atatgccctg ccccaccta    120 actgatgaca ttccaccaca aaacaagtgt aaatggccgg tccttgcctt aactgatgac    180
attaccttgt gaaagtcctt ttcctggctc atcctggctc aaaagcaccc ccactgagca    240
ccttgcgacc cccactcctg cccgccagag aacaaacccc ctttgactgt aattttcctt    300
tacctaccca aatcctataa aacggcccca cccttaactc ccttcactga ctctcttttc    360
ggactcagcc cacctgtacc caggtgatta aaagctttat tgctcacaca aacctgttt    420 ggtggtctct tcacacggac gcgcatgaaa                                    450
```

<210> SEQ ID NO 8
<211> LENGTH: 29
<212> TYPE: DNA
<213> ORGANISM: Artificial Sequence
<220> FEATURE:
<223> OTHER INFORMATION: PCR primer

<400> SEQUENCE: 8

```
tgtgaaagtt ttttttttgg tttattttg                                      29
```

<210> SEQ ID NO 9
<211> LENGTH: 27
<212> TYPE: DNA
<213> ORGANISM: Artificial Sequence
<220> FEATURE:
<223> OTHER INFORMATION: PCR primer

<400> SEQUENCE: 9
cctctccaaa actctaatac atatctt                                27

<210> SEQ ID NO 10
<211> LENGTH: 24
<212> TYPE: DNA
<213> ORGANISM: Artificial Sequence
<220> FEATURE:
<223> OTHER INFORMATION: sequencing primer

<400> SEQUENCE: 10
acaataaaac tatttatttc acct                                   24

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
aaagtttgtt tggtggtttt tt                                     22

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12
aaaaaaatta atctcctcca tatacctt                               28

<210> SEQ ID NO 13
<211> LENGTH: 19
<212> TYPE: DNA
<213> ORGANISM: Artificial Sequence
<220> FEATURE:
<223> OTHER INFORMATION: sequencing primer

<400> SEQUENCE: 13
ttgtttggtg gttttttta                                         19

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
tgtgtattaa tgtatggtta attttggtaa                             30

<210> SEQ ID NO 15
<211> LENGTH: 26
<212> TYPE: DNA
<213> ORGANISM: Artificial Sequence
<220> FEATURE:
<223> OTHER INFORMATION: PCR primer

```
<400> SEQUENCE: 15
caaaccatct aaacaaatac ctacaa                                          26

<210> SEQ ID NO 16
<211> LENGTH: 21
<212> TYPE: DNA
<213> ORGANISM: Artificial Sequence
<220> FEATURE:
<223> OTHER INFORMATION: sequencing primer

<400> SEQUENCE: 16 gttgttttt atgtagtgtt t                                                21

<210> SEQ ID NO 17
<211> LENGTH: 23
<212> TYPE: DNA
<213> ORGANISM: Artificial Sequence
<220> FEATURE:
<223> OTHER INFORMATION: sequencing primer

<400> SEQUENCE: 17
ttaggttttt gagtttaagt taa                                             23

<210> SEQ ID NO 18
<211> LENGTH: 29
<212> TYPE: DNA
<213> ORGANISM: Artificial Sequence
<220> FEATURE:
<223> OTHER INFORMATION: PCR primer

<400> SEQUENCE: 18
aagtttgttt ggtggttttt ttatataga                                       29

<210> SEQ ID NO 19
<211> LENGTH: 29
<212> TYPE: DNA
<213> ORGANISM: Artificial Sequence
<220> FEATURE:
<223> OTHER INFORMATION: PCR primer

<400> SEQUENCE: 19
accattccac aatcataata aaatacttt                                       29

<210> SEQ ID NO 20
<211> LENGTH: 23
<212> TYPE: DNA
<213> ORGANISM: Artificial Sequence
<220> FEATURE:
<223> OTHER INFORMATION: sequencing primer

<400> SEQUENCE: 20
accaataaca ataaacaaaa ttt                                             23

<210> SEQ ID NO 21
<211> LENGTH: 28
<212> TYPE: DNA
<213> ORGANISM: Artificial Sequence
<220> FEATURE:
<223> OTHER INFORMATION: PCR primer

<400> SEQUENCE: 21
gttgtggagt tatttagatt tgggttta                                        28

<210> SEQ ID NO 22
```

```
<211> LENGTH: 28
<212> TYPE: DNA
<213> ORGANISM: Artificial Sequence
<220> FEATURE:
<223> OTHER INFORMATION: PCR primer

<400> SEQUENCE: 22
cttttcctac catacataac actttaac                                      28

<210> SEQ ID NO 23
<211> LENGTH: 19
<212> TYPE: DNA
<213> ORGANISM: Artificial Sequence
<220> FEATURE:
<223> OTHER INFORMATION: sequencing primer

<400> SEQUENCE: 23 tttttttatta aggggttgg                                               19

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24
tttttttttt gaaggtgagg gaaagtagtt                                    30

<210> SEQ ID NO 25
<211> LENGTH: 29
<212> TYPE: DNA
<213> ORGANISM: Artificial Sequence
<220> FEATURE:
<223> OTHER INFORMATION: PCR primer

<400> SEQUENCE: 25
aacctataaa tctccatttc tctcatctc                                     29

<210> SEQ ID NO 26
<211> LENGTH: 15
<212> TYPE: DNA
<213> ORGANISM: Artificial Sequence
<220> FEATURE:
<223> OTHER INFORMATION: sequencing primer

<400> SEQUENCE: 26
tggtaggaat ggggt                                                    15

<210> SEQ ID NO 27
<211> LENGTH: 29
<212> TYPE: DNA
<213> ORGANISM: Artificial Sequence
<220> FEATURE:
<223> OTHER INFORMATION: PCR primer

<400> SEQUENCE: 27
ggataatttg aaaatgtttt tggttaagg                                     29

<210> SEQ ID NO 28
<211> LENGTH: 29
<212> TYPE: DNA
<213> ORGANISM: Artificial Sequence
<220> FEATURE:
<223> OTHER INFORMATION: PCR primer

<400> SEQUENCE: 28
```
ataattcttc aattacttca aaccatcta                                          29

<210> SEQ ID NO 29
<211> LENGTH: 21
<212> TYPE: DNA
<213> ORGANISM: Artificial Sequence
<220> FEATURE:
<223> OTHER INFORMATION: sequencing primer

<400> SEQUENCE: 29
ggtttttgag tttaagttaa g                                                  21

<210> SEQ ID NO 30
<211> LENGTH: 30
<212> TYPE: DNA
<213> ORGANISM: Artificial Sequence
<220> FEATURE:
<223> OTHER INFORMATION: PCR primer

<400> SEQUENCE: 30
tttttttttt ggtttatttt ggtttaaaag                                         30

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
acaaaccata tctcaaataa aaaatttcat                                         30

<210> SEQ ID NO 32
<211> LENGTH: 20
<212> TYPE: DNA
<213> ORGANISM: Artificial Sequence
<220> FEATURE:
<223> OTHER INFORMATION: sequencing primer

<400> SEQUENCE: 32
atataaaatt tgtttggtgg                                                    20

<210> SEQ ID NO 33
<211> LENGTH: 340
<212> TYPE: DNA
<213> ORGANISM: Homo sapiens

<400> SEQUENCE: 33
tgtgaaagtc ctcttcctgg ctcatcctgg ctcaaaaagc accccactg agcaccttga         60 gaccccact cctgcccgcc agagaacaaa cccccttga ctgtaatttt cctttaccta         120
cccaaatcct ataaaacggc cccacccctta tctcccttca ctgactctct tttcggactc      180
agcccgcctg cacccaggtg aaataaacag cttattgct cacacaaagc ctgtttggtg        240
gtctcttcac acggacgcac atgaaattta gttgtatcca taaggcatat ggaggagact       300
aattcctctt ccaaagacat gtaccagagt cctggagagg                             340

<210> SEQ ID NO 34
<211> LENGTH: 84
<212> TYPE: DNA
<213> ORGANISM: Homo sapiens

<400> SEQUENCE: 34

```
aaagcctgtt tggtggtctc ttcacacgga cgcacatgaa atttagttgt atccataagg      60
catatggagg agactaattc ctct                                              84

<210> SEQ ID NO 35
<211> LENGTH: 196
<212> TYPE: DNA
<213> ORGANISM: Homo sapiens

<400> SEQUENCE: 35
tgtgtaccaa tgtatggtca attttggcaa attttccata tgcttgaaaa gaatgtgttc      60
tgctgttttt catgcagtgt tctatgtacg tcgattgaat cgggattatt aaccatgctt     120
aaatttgtca ggcctctgag cccaagccaa gccatcgcat ccctgtgac ttgcaggtat      180 ctgcccagat ggcctg                                                      196

<210> SEQ ID NO 36
<211> LENGTH: 135
<212> TYPE: DNA
<213> ORGANISM: Homo sapiens

<400> SEQUENCE: 36
aagcctgttt ggtggtctct tcacacagac gcgcatgaaa aaattttgtc tattgttact      60
ggttttttgg actgcttgct ttttcagtta ctcaaagagg attattaaag tacctcatca     120
tgattgtgga atggt                                                       135

<210> SEQ ID NO 37
<211> LENGTH: 267
<212> TYPE: DNA
<213> ORGANISM: Homo sapiens

<400> SEQUENCE: 37
gctgtggagc cactcagact tgggttcaaa tctgtccttg ccacatacc ctttgtgacc       60 ttggtaaatt gttctcccct aagttttccc atttttttac caaggggttg gcgaagacca     120
ctgcacaggg ttgttgtgaa gactgaatta agtaagataa tgtatgtaaa gtacccagct     180
gctagtaagc actagacaaa tacttgttcc tttccgtccc tctttctgtt acaaattagg     240
ctaaagtgtt atgtatggca ggaaaag                                          267

<210> SEQ ID NO 38
<211> LENGTH: 236
<212> TYPE: DNA
<213> ORGANISM: Homo sapiens

<400> SEQUENCE: 38
cttctttctt gaaggtgagg gaaagcagtt aggaaacaga gcgaggaaca ggtgaatgtt      60
aactcagacc cctggcagga atggggctgt tctacgttat aaactgcctg agagttaata    120
gaggacttcc acacaagtct ttcgcactcg ttattctttt aaatcctcac agcaactctc    180
tgagtttgtc atcattgctt ccacttagag atgagagaaa tggagaccta taggtt         236

<210> SEQ ID NO 39
<211> LENGTH: 201
<212> TYPE: DNA
<213> ORGANISM: Homo sapiens

<400> SEQUENCE: 39 ggataaatttg aaaatgccct tggccaaggg gaagctccac cagtcagttg ggggagctta     60
gaattttatt tttggtttac aagttcatta tatattttgg atattaactc cttgtcaggc    120
```

```
ctctgagccc aagccaagcc atcgcatccc ctgtgacttg cacatatacg cccagatggc      180
ctgaagtaac tgaagaatca c                                                201

<210> SEQ ID NO 40
<211> LENGTH: 279
<212> TYPE: DNA
<213> ORGANISM: Homo sapiens

<400> SEQUENCE: 40 tcctttcct ggctcatcct ggctcaaaag caccccact gagcaccttg cgaccccac         60 tcctgcccgc cagagaacaa acccccttg actgtaattt tcctttacct acccaaatcc      120
tataaaacgg ccccacccttt aactcccttc actgactctc ttttcggact cagcccacct    180
gtacccaggt gattaaaagc tttattgctc acacaaaacc tgtttggtgg tctcttcaca    240
cggacgcgca tgaaactcct tatctgagat atggtttgc                            279
```

METHOD FOR SCREENING INDUCED PLURIPOTENT STEM CELLS

CROSS-REFERENCE TO RELATED APPLICATIONS

This application is a Divisional of co-pending application Ser. No. 14/235,391 filed Jun. 2, 2014, which is the National Phase of PCT/JP2012/004747 filed on Jul. 25, 2012, which claims the benefit under 35 U.S.C. 119(e) to U.S. Provisional Application No. 61/511,156 filed on Jul. 25, 2011, all of which are hereby expressly incorporated by reference into the present application.

TECHNICAL FIELD

The present invention relates to a method for screening induced pluripotent stem cells. More specifically, the present invention relates to a method for screening induced pluripotent stem cells exhibiting no differentiation resistance through confirmation of the expression of large intergenic non-coding RNA (lincRNA) or mRNA in induced pluripotent stem cells.

BACKGROUND ART

In recent years, mouse and human induced pluripotent stem cells (iPS cells) have been successively established. Yamanaka et al., have induced iPS cells by introducing Oct3/4, Sox2, Klf4, and c-Myc genes into mouse-derived fibroblasts so as to enable the forced expression of such genes (WO 2007/069666 A1 and Takahashi, K. and Yamanaka, S., Cell, 126: 663-676 (2006)). Subsequently, it has been revealed that iPS cells can also be prepared using 3 of the above factors (excluding the c-Myc gene) (Nakagawa, M. et al., Nat. Biotechnol., 26: 101-106 (2008)). Furthermore, Yamanaka et al., have succeeded in establishing iPS cells by introducing the 4 above genes into human skin-derived fibroblasts, similarly to the case involving mice (WO 2007/069666 A1 and Takahashi, K. et al., Cell, 131: 861-872 (2007)). Meanwhile, Thomson et al.,'s group has prepared human iPS cells using Nanog and Lin28 instead of Klf4 and c-Myc (WO 2008/118820 A2 and Yu, J. et al., Science, 318: 1917-1920 (2007)). iPS cells can solve bioethical issues such as embryo disruption, and can be grown while maintaining their pluripotency, so that iPS cells are expected as grafting materials for regenerative medicine.

Meanwhile, even when the thus established iPS cells are induced to differentiate into specific tissue cells, the resulting cells may include undifferentiated (or insufficiently differentiated) cells having proliferation potency (Miura K. et al., Nat Biotechnol., 27: 743-745 (2009)). In such a case, there are concerns about tumorigenesis after grafting. Hence, a method for screening for an iPS cell line containing no cells that exhibit resistance to differentiation induction from among the thus established iPS cell lines has been desired.

SUMMARY OF INVENTION

Technical Problem

An object of the invention is to efficiently select safe iPS cells (induced pluripotent stem cells) suitable for clinical applications. Specifically, an object of the invention is to provide a means for screening for a cell line exhibiting no differentiation resistance.

Solution to Problem

To achieve the above objects, the present inventors have examined RNA that is specifically expressed in iPS cell lines exhibiting differentiation resistance or RNA that is specifically expressed in iPS cell lines exhibiting no differentiation resistance using iPS cell lines exhibiting differentiation resistance and iPS cell lines exhibiting no differentiation resistance. It was thus confirmed that large intergenic non-coding RNA (lincRNA) or mRNA encoded by a specific genomic region is specifically expressed in iPS cell lines exhibiting differentiation resistance or iPS cell lines exhibiting no differentiation resistance.

Based on the above results, the present inventors have discovered that iPS cells exhibiting differentiation resistance can be screened for through the use of large intergenic non-coding RNA (lincRNA) or mRNA encoded by a specific genomic region as an indicator (marker), and thus have completed the present invention.

Specifically, the present invention includes the following [1] to [9].

[1] A method for screening for a human induced pluripotent stem cell line exhibiting no differentiation resistance, comprising the steps of:
(i) measuring expression of at least one large intergenic non-coding RNA (lincRNA) or mRNA selected from group A and/or group B,
(ii) selecting a human induced pluripotent stem cell line in which the lincRNA or mRNA selected from group A expresses or the lincRNA or mRNA selected from group B does not express;
Group A consisting of
(A1) lincRNA:chr1:852245-854050 reverse strand,
(A2) GPR177,
(A3) VTCN1,
(A4) lincRNA:chr1:142803013-142804254 reverse strand,
(A5) APOA2,
(A6) WNT6,
(A7) EPAS1,
(A8) COL3A1,
(A9) SLC40A1,
(A10) S100P,
(A11) HOPX,
(A12) GUCY1A3,
(A13) CDH10,
(A14) HAPLN1,
(A15) PITX1,
(A16) HAND1,
(A17) CGA,
(A18) AQP1,
(A19) DLX6,
(A20) DLX5,
(A21) SOX17,
(A22) FLJ45983,
(A23) PLCE1,
(A24) H19,
(A25) lincRNA:chr11:2016408-2017024 reverse strand,
(A26) lincRNA:chr11:2017517-2017651 forward strand,
(A27) IGF2,
(A28) P2RY6,
(A29) SLN,
(A30) NNMT,
(A31) APOA1,
(A32) ERP27,
(A33) LUM,
(A34) CCDC92,
(A35) CDX2, (A36) FLJ41170,
(A37) MEG3,
(A38) lincRNA:chr14:101292469-101299626 forward strand,
(A39) lincRNA:chr14:101295637-101302637 forward strand,
(A40) lincRNA:chr14:101296681-101298460 forward strand,
(A41) lincRNA:chr14:101298129-101300147 forward strand,
(A42) lincRNA:chr14:101324825-101327247 forward strand,
(A43) MEG8,
(A44) lincRNA:chr14:101365673-101366049 forward strand,
(A45) lincRNA:chr14:101396955-101397357 forward strand,
(A46) lincRNA:chr14:101430757-101433381 forward strand,
(A47) lincRNA:chr14:101434059-101436282 forward strand,
(A48) lincRNA:chr14:101472355-101473369 forward strand,
(A49) DIO3,
(A50) MEIS2,
(A51) PRTG,
(A52) C17orf51,
(A53) lincRNA:chr17:21434064-21435857 reverse strand,
(A54) lincRNA:chr17:21435180-21454915 reverse strand,
(A55) lincRNA:chr17:21435959-21436405 reverse strand,
(A56) CCR7,
(A57) KRT23,
(A58) GREB1L,
(A59) GATA6,
(A60) TTR,
(A61) UCA1,
(A62) FLRT3,
(A63) lincRNA:chrX:73040495-73047819 reverse strand,
(A64) VGLL1,
(A65) RPS4Y1,
(A66) DDX3Y, and
(A67) RPS4Y2,
Group B consisting of
(B1) DMRTB1,
(B2) lincRNA:chr1:73430887-73446112 reverse strand,
(B3) lincRNA:chr1:73444697-73444997 reverse strand,
(B4) C4orf51,
(B5) PCDHA1,
(B6) lincRNA:chr6:95250854-95263604 reverse strand,
(B7) lincRNA:chr6: 14280358-14285376 reverse strand,
(B8) lincRNA:chr6:14283301-14285685 reverse strand,
(B9) C7orf57,
(B10) lincRNA:chr7:124873114-124899839 reverse strand,
(B11) lincRNA:chr8: 129599518-129624118 reverse strand,
(B12) OC90,
(B13) lincRNA:chr8:133071643-133092468 reverse strand,
(B14) lincRNA:chr8: 133073732-133075753 reverse strand,
(B15) HHLA1,
(B16) lincRNA:chr8:133076031-133093351 reverse strand,
(B17) lincRNA:chr8: 133090096-133097869 reverse strand,
(B18) lincRNA:chr8: 138387843-138421643 reverse strand,
(B19) lincRNA:chr8: 138418343-138425831 reverse strand,
(B20) NDUFA4L2,
(B21) lincRNA:chr13:54698462-54707001 reverse strand,
(B22) ABHD12B,
(B23) lincRNA:chr18:54721302-54731677 reverse strand,
(B24) ZNF208,
(B25) ZNF257,
(B26) ZNF676,
(B27) ZNF541,
(B28) TBX1,
(B29) CXorf61, and
(B30) DB090170 TESTI4 *Homo sapiens* cDNA clone TESTI4038997-5', mRNA sequence [DB090170].

[2] The method according to [1], wherein the lincRNA or mRNA selected from group A is selected from the group consisting of
(A20) DLX5,
(A50) MEIS2,
(A53) lincRNA:chr17:21434064-21435857 reverse strand, and
(A58) GREB1L.

[3] The method according to [1], wherein the lincRNA or mRNA selected from group B is selected from the group consisting of
(B4) C4orf51,
(B9) C7orf57,
(B10) lincRNA:chr7:124873114-124899839 reverse strand,
(B12) OC90,
(B13) lincRNA:chr8:133071643-133092468 reverse strand,
(B14) lincRNA:chr8:133073732-133075753 reverse strand,
(B15) HHLA1,
(B16) lincRNA:chr8:133076031-133093351 reverse strand,
(B17) lincRNA:chr8:133090096-133097869 reverse strand,
(B22) ABHD12B,
(B23) lincRNA:chr18:54721302-54731677 reverse strand,
(B27) ZNF541,
(B28) TBX1,
(B29) CXorf61, and
(B30) DB090170 TESTI4 *Homo sapiens* cDNA clone TESTI4038997 5', mRNA sequence [DB090170].

[4] The method according to [1], wherein the lincRNA or mRNA selected from group B is selected from the group consisting of;
(B4) C4orf51,
(B15) HHLA1, and
(B22) ABHD12B.

[5] A method for screening for a human induced pluripotent stem cell line exhibiting no differentiation resistance, comprising the following steps;
(i) measuring DNA-methylated state of LTR region or neighborhood thereof located in at least one gene selected from group of (B4) C4orf51, (B15) HHLA1, and (B22) ABHD12B, and
(ii) selecting a human induced pluripotent stem cell line in which the LTR7 region is in a DNA-methylated state.

[6] A reagent for screening for a human induced pluripotent stem cell line exhibiting no differentiation resistance, containing a polynucleotide having at least 15 continuous nucleotides in the nucleotide sequence of at least one mRNA or LincRNA shown in the above group A or B, or a polynucleotide complementary thereto.

[7] The reagent according to [6], which is a microarray prepared by immobilizing, as a probe, a polynucleotide complementary to a polynucleotide having at least 15 continuous nucleotides in the nucleotide sequence of at least one mRNA or LincRNA shown in the above group A or B.

[8] A reagent for screening for a human induced pluripotent stem cell line exhibiting no differentiation resistance, containing an antibody that recognizes a protein encoded by at least one mRNA shown in the above group A or B.

[9] A kit for screening for a human induced pluripotent stem cell line exhibiting no differentiation resistance, containing the reagent according to any one of [6] to [8].

The present application claims priority from the U.S. Provisional Application No. 61/511,156 filed on Jul. 25, 2011, and the contents of these patent applications are herein incorporated by reference.

Advantageous Effects of Invention

According to the present invention, human iPS cells exhibiting no differentiation resistance can be efficiently screened for. Therefore, the present invention is extremely useful for application of iPS cells to regenerative medicine.

BRIEF DESCRIPTION OF DRAWINGS

FIG. 1 shows the result of measuring expression level of HHLA1, ABHD12B and C4orf51 of cell lines exhibiting differentiation resistance (shown as differentiation resistance): FB-RV3F-4, CB-RV4F-2, DP-EP6F-1, FB-RV3F-4 sub2, CB-RV4F-2 sub2 and DP-EP6F-1, and cell lines exhibiting no differentiation resistance (shown as normal): H1, FB-RV4F-2, FB-RV3F-1, FB-RV3F-4 sub6, CB-RV4F-2 sub1 and DP-EP6F-1 sub5, with quantitative PCR.

FIG. 2 is a schematic diagram showing locations of LTR region in C4orf51, HHLA1 and ABHD12B.

FIG. 3 shows the results of the average methylation state of CG dinucleotide in LTR7 region located in C4orf51, HHLA1 or ABHD12B of 6 cell lines exhibiting differentiation resistance (shown as differentiation resistance): FB-RV3F-4, CB-RV4F-2, DP-EP6F-1, FB-RV3F-4 sub2, CB-RV4F-2 sub2 and DP-EP6F-1, and 6 cell lines exhibiting no differentiation resistance (shown as normal): H1, FB-RV4F-2, FB-RV3F-1, FB-RV3F-4 sub6, CB-RV4F-2 sub1 and DP-EP6F-1 sub5, by the Bisulfite method.

DESCRIPTION OF EMBODIMENTS

1. Method for Screening Human Induced Pluripotent Stem Cells (iPS Cells)

The method for screening human induced pluripotent stem cells (iPS cells) of the present invention comprises using at least one lincRNA or mRNA shown in the following Table 1 (Group A) or 2 (Group B) as a marker for screening for an iPS cell line exhibiting no differentiation resistance.

TABLE 1

| Group A | |
| --- | --- |
| Marker name | Genbank Accession |
| lincRNA:chr1:852245-854050 reverse strand | |
| GPR177 | NM_001002292 |
| VTCN1 | NM_024626 |
| lincRNA:chr1:142803013-142804254 reverse strand | |
| APOA2 | NM_001643 |
| WNT6 | NM_006522 |
| EPAS1 | NM_001430 |
| COL3A1 | NM_000090 |
| SLC40A1 | NM_014585 |
| S100P | NM_005980 |
| HOPX | NM_139211 |
| GUCY1A3 | NM_000856 |
| CDH10 | NM_006727 |
| HAPLN1 | NM_001884 |
| PITX1 | NM_002653 |
| HAND1 | NM_004821 |
| CGA | NM_000735 |
| AQP1 | NM_198098 |

TABLE 1-continued

| Group A | |
| --- | --- |
| Marker name | Genbank Accession |
| DLX6 | NM_005222 |
| DLX5 | NM_005221 |
| SOX17 | NM_022454 |
| FLJ45983 | NR_024256 |
| PLCE1 | NM_016341 |
| H19 | NR_002196 |
| lincRNA:chr11:2016408-2017024 reverse strand | |
| lincRNA:chr11:2017517-2017651 forward strand | |
| IGF2 | NM_000612 |
| P2RY6 | NM_176798 |
| SLN | NM_003063 |
| NNMT | NM_006169 |
| APOA1 | NM_000039 |
| ERP27 | NM_152321 |
| LUM | NM_002345 |
| CCDC92 | NM_025140 |
| CDX2 | NM_001265 |
| FLJ41170 | AK021542 |
| MEG3 | NR_003530 |
| lincRNA:chr14:101292469-101299626 forward strand | |
| lincRNA:chr14:101295637-101302637 forward strand | |
| lincRNA:chr14:101296681-101298460 forward strand | |
| lincRNA:chr14:101298129-101300147 forward strand | |
| lincRNA:chr14:101324825-101327247 forward strand | |
| MEG8 | NR_024149 |
| lincRNA:chr14:101365673-101366049 forward strand | |
| lincRNA:chr14:101396955-101397357 forward strand | |
| lincRNA:chr14:101430757-101433381 forward strand | |
| lincRNA:chr14:101434059-101436282 forward strand | |
| lincRNA:chr14:101472355-101473369 forward strand | |
| DIO3 | NM_001362 |
| MEIS2 | NM_170677 |
| PRTG | NM_173814 |
| C17orf51 | NM_001113434 |
| lincRNA:chr17:21434064-21435857 reverse strand | |
| lincRNA:chr17:21435180-21454915 reverse strand | |
| lincRNA:chr17:21435959-21436405 reverse strand | |
| CCR7 | NM_001838 |
| KRT23 | NM_015515 |
| GREB1L | NM_001142966 |
| GATA6 | NM_005257 |
| TTR | NM_000371 |
| UCA1 | NR_015379 |
| FLRT3 | NM_198391 |
| lincRNA:chrX:73040495-73047819 reverse strand | |
| VGLL1 | NM_016267 |
| RPS4Y1 | NM_001008 |
| DDX3Y | NM_001122665 |
| RPS4Y2 | NM_001039567 |

TABLE 2

Group B

| Marker name | Genbank Accession |
| --- | --- |
| DMRTB1 | NM_033067 |
| lincRNA:chr1:73430887-73446112 reverse strand | |
| lincRNA:chr1:73444697-73444997 reverse strand | |
| C4orf51 | NM_001080531 |
| PCDHA1 | NM_031410 |
| lincRNA:chr6:95250854-95263604 reverse strand | |
| lincRNA:chr6:14280358-14285376 reverse strand | |
| lincRNA:chr6:14283301-14285685 reverse strand | |
| C7orf57 | NM_001100159 |
| lincRNA:chr7:124873114-124899839 reverse strand | |
| lincRNA:chr8:129599518-129624118 reverse strand | |
| OC90 | NM_001080399 |
| lincRNA:chr8:133071643-133092468 reverse strand | |
| lincRNA:chr8:133073732-133075753 reverse strand | |
| HHLA1 | NM_001145095 |
| lincRNA:chr8:133076031-133093351 reverse strand | |
| lincRNA:chr8:133090096-133097869 reverse strand | |
| lincRNA:chr8:138387843-138421643 reverse strand | |
| lincRNA:chr8:138418343-138425831 reverse strand | |
| NDUFA4L2 | NM_020142 |
| lincRNA:chr13:54698462-54707001 reverse strand | |
| ABHD12B | NM_181533 |
| lincRNA:chr18:54721302-54731677 reverse strand | |
| ZNF208 | NM_007153 |
| ZNF257 | NM_033468 |
| ZNF676 | NM_001001411 |
| ZNF541 | NM_001101419 |
| TBX1 | NM_080647 |
| CXorf61 | NM_001017978 |
| DB090170 TESTI4 *Homo sapiens* cDNA clone TESTI4038997 5', mRNA sequence | DB090170 |

In the present invention, the term "lincRNA" refers to long-chain single-stranded RNA transcribed from a genome, which encodes no gene. LincRNA is denoted with chromosome No., the genome region represented by nucleotide No. described in the GenBank database, and transcriptional direction. For example, "chr1:852245-854050 reverse strand" means single-stranded RNA matching a sequence complementary to nucleotides 852245 to 854050 of chromosome 1 in the GenBank database.

In the present invention, the term "mRNA" may also refer to a precursor before splicing or mature mRNA after splicing. Examples of the sequence of mature mRNA include not only mRNAs having sequences corresponding to Accession Nos. of GenBank listed in Table 1 or 2, but also isoforms prepared by selective splicing. Also in the present invention, a polynucleotide (e.g., cDNA) from the mRNA or a protein encoded by the RNA can also be used as a marker.

Furthermore, in the present invention, the term "iPS cells" refers to stem cells artificially derived from somatic cells, which can be prepared by introducing a specific reprogramming factor in the form of DNA or protein into somatic cells and have properties almost equivalent to those of ES cells, such as pluripotency and proliferation potency based on self-replication (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26: 101-106 (2008); International Publication WO 2007/069666).

In the present invention, lincRNA or mRNA that can be recognized as a marker may be a polynucleotide comprising the full-length nucleotide sequence of the lincRNA or mRNA, a polynucleotide comprising a sequence complementary thereto, or, a fragment thereof. In the case of such a polynucleotide fragment, it preferably has a polynucleotide having at least 15 continuous nucleotides in the sequence of the lincRNA or mRNA. Specific examples of such a polynucleotide having at least 15 nucleotides include a polynucleotide having a length of at least 18 continuous nucleotides, a polynucleotide having a length of at least 19 continuous nucleotides, a polynucleotide having a length of at least 20 continuous nucleotides, a polynucleotide having a length of at least 30 continuous nucleotides, a polynucleotide having a length of at least 40 continuous nucleotides, a polynucleotide having a length of at least 50 continuous nucleotides, a polynucleotide having a length of at least 60 continuous nucleotides, a polynucleotide having a length of at least 70 continuous nucleotides, and a polynucleotide having a length of at least 100 continuous nucleotides.

In the present invention, an iPS cell line exhibiting no differentiation resistance can be detected by measuring the degree of the expression of the above marker, and thus the iPS cell line can be screened for. More specifically, an iPS cell line expressing a marker of group A listed in Table 1 can be screened for as a cell line exhibiting no differentiation resistance, or an iPS cell line not expressing a marker of group B listed in Table 2 can be screened for as a cell line exhibiting no differentiation resistance.

Here, the expression "expressing a marker" refers to a situation in which a marker is detected by an arbitrary measuring method, and more preferably to a situation in which the thus obtained detection value is equivalent to or higher than a control detection value. Similarly, the expression "not expressing a marker" refers to a situation in which no marker is detected by an arbitrary measuring method, and more preferably to a situation in which the thus obtained detection value is equivalent to or lower than a control detection value. More specifically, when a marker of group A is used, a case in which a detection value is similar to that of a control ES cell line or an iPS cell line known to exhibit no differentiation resistance or a case in which a detection value is higher than that of an iPS cell line known to exhibit differentiation resistance indicates that a marker of group A is expressed. Meanwhile, when a marker of group B is used, a case in which the thus obtained detection value is similar to that of a control ES cell line or an iPS cell line known to exhibit no differentiation resistance or a case in which the thus obtained detection value is lower than that of an iPS cell line known to exhibit differentiation resistance indicates that a marker of group B is not expressed. Here, the expression "detection value high(er)" refers to a situation in which a detection value is 1.5 times, 2 times, 3 times, 4 times, or 5 times higher than a control value, for example, and more preferably, 5 or more times higher than the control value. The expression "detection value lower" refers to a situation in which a detection value is ⅔, ½, ⅓, ¼, or ⅕ (or less) of the control value, for example, and more preferably, ⅕ (or less) of the control value.

In the present invention, examples of a method for measuring a marker include, but are not particularly limited to, a Northern blot method, in situ hybridization, RNase protection assay, a microarray method, a PCR method, a real-time PCR method, a Western blot method, and flow cytometry.

In the case of a measuring method using hybridization, such as the Northern blot method, the full-length nucleotide sequence of the above marker or a polynucleotide complementary to a partial sequence thereof can be used as a probe. Here, the term "complementary polynucleotide (complementary strand, opposite strand)" refers to a polynucleotide that is in a complementary relationship with a subject sequence in terms of nucleotides on the basis of a base pair relationship such as A:T(U) or G:C. Examples of such a complementary strand include not only a complementary sequence completely complementary to the nucleotide sequence of a subject forward strand, but also a sequence having a complementary relationship such that it can hybridize to a subject forward strand under stringent conditions. In addition, stringent conditions can be determined based on the melting temperature (Tm) of a nucleic acid to be bound with a probe, as taught by Berger and Kimmel (1987, Guide to Molecular Cloning Techniques Methods in Enzymology, Vol. 152, Academic Press, San Diego Calif.). Washing conditions after hybridization are generally conditions of about "1×SSC, 0.1% SDS, 37 degrees C.," for example. Preferably a complementary strand can maintain a state of hybridizing to a subject forward strand even when washed under such conditions. Examples of even more stringent hybridization conditions include, but are not particularly limited to, washing conditions of about "0.5×SSC, 0.1% SDS, 42 degrees C." Examples of more stringent hybridization conditions include conditions under which a forward strand and the complementary strand can maintain the hybridization state even when washed under washing conditions of about "0.1×SSC, 0.1% SDS, 65 degrees C." Specific examples of such a complementary strand include a strand consisting of a nucleotide sequence that is in a complete complementary relationship with a subject forward-strand nucleotide sequence, and a strand consisting of a nucleotide sequence having at least 90%, preferably at least 95%, 96%, 97%, 98%, or 99% sequence identity with the strand. The probe size is a length of at least 15 continuous nucleotides, at least 18 continuous nucleotides, at least 19 continuous nucleotides, at least 20 continuous nucleotides, at least 30 continuous nucleotides, at least 40 continuous nucleotides, at least 50 continuous nucleotides, at least 60 continuous nucleotides, at least 70 continuous nucleotides, at least 100 continuous nucleotides, or full-length continuous nucleotides. Such a probe may be labeled with a radioisotope (e.g., 32P and 33P), a fluorescent substance (e.g., fluorescamine, rhodamine, Texas Red, dansyl, or derivatives thereof), a chemiluminescent substance, or an enzyme, for example.

Furthermore, a poly(oligo)nucleotide serving as the above probe is preferably provided in the form of a microarray with the poly(oligo)nucleotide immobilized on a solid-phase support (substrate). Examples of a solid-phase support for a microarray include a glass substrate, a silicon substrate, a membrane, and beads, but the material, size, and shape thereof are not particularly limited. A method for forming a microarray is not particularly limited, and any method that can be used by persons skilled in the art may be employed herein. Examples thereof include a method (on-chip method) that involves directly synthesizing a probe on the surface of a solid-phase support and a method that involves binding a probe prepared in advance to the surface of a solid-phase support. A method that is generally employed when a probe is directly synthesized on the surface of a solid-phase support comprises performing selective synthesis of an oligonucleotide in a predetermined micro-matrix region using a protecting group to be selectively removed by light irradiation in combination with a photolithographic technique and a solid phase synthesis technique that are used for semiconductor manufacturing. Meanwhile, examples of a method that can be used herein, which comprises preparing a probe in advance and then binding it to the surface of a solid-phase support, include a method that comprises spotting a probe onto the surface of a solid-phase support that has been surface-treated with a polycationic compound or a silane coupling agent having an amino group, an aldehyde group, an epoxy group or the like using a spotter device depending on nucleic acid probe types or solid-phase support types, and a method that comprises synthesizing a probe having a reactive group introduced therein, spotting the probe onto the surface of a solid-phase support that has been surface-treated in advance so as to cause the formation of a reactive group, and thus binding and immobilizing the probe onto the surface of the solid-phase support via covalent bonding.

In another embodiment, when the above marker is specifically recognized and amplified, an oligonucleotide containing a nucleotide sequence of the marker or a sequence complementary to the nucleotide sequence can be used as a primer. A primer can be prepared by designing it based on each nucleotide sequence of the above marker using primer 3 (http://primer3.sourceforge.net/) or vector NTI (Infomax), for example, and then performing synthesis and purification. A primer is designed while avoiding a complementary sequence of the two primers so as to prevent a set of or a pair of primers (2 primers) consisting of a sense strand (5' terminal side) and an antisense strand (3' terminal side) from annealing to each other; and also avoiding palindrome so as to prevent the formation of a hairpin structure within a primer. The primer size is not particularly limited, as long as amplification and detection of the above marker are possible, and is a length of at least 15 nucleotides, preferably a length of 15 to 50 nucleotides, and more preferably a length of 20 to 35 nucleotides. A primer can be synthesized with a method known in the art as a method for synthesizing an oligonucleotide (e.g., a phosphotriethyl method and a phosphodiester method) using a generally employed automatic DNA synthesizer. Such a primer may be labeled with a labeling substance similar to the above so as to facilitate the detection of amplification products.

In another embodiment, an antibody can be used when the above marker is recognized as a protein.

The form of the antibody of the present invention is not particularly limited and may be a polyclonal antibody or a monoclonal antibody the immunogen of which is a protein encoded by mRNA listed in Table 1 or 2, or, a chimeric antibody (e.g., a human/mouse chimeric antibody), a humanized antibody, or a human antibody, or, a fragment of these antibodies (e.g., Fab, Fab', F(ab')2, Fc, Fv, and scFv), or, an antibody having antigen-binding property to a polypeptide comprising at least 8 continuous amino acids (e.g., 10 to 20 continuous amino acids) in the amino acid sequence of the protein.

Methods for producing the above antibody are known and the antibody of the present invention can be produced according to these conventional methods (Current protocols in Molecular Biology edit. Ausubel et al., (1987) Publish. John Wiley and Sons. Section 11.12-11.13).

Specifically, when the antibody of the present invention is a polyclonal antibody, it can be obtained by synthesizing a protein encoded by mRNA listed in Table 1 or 2, which has been expressed and purified according to a conventional method using *Escherichia coli* or the like, or an oligopeptide having a partial amino acid sequence thereof, immunizing a non-human animal such as a domestic rabbit with the resultant, and then obtaining the antibody from the serum of the immunized animal according to a conventional method. Meanwhile, in the case of a monoclonal antibody, it can be obtained by subjecting hybridoma cells (prepared by cell fusion of myeloma cells with spleen cells obtained from the above-immunized non-human animal) to HAT selection and affinity assay with a target polypeptide (Current protocols in Molecular Biology edit. Ausubel et al., (1987) Publish. John Wiley and Sons. Section 11.4-11.11), for example. The thus obtained antibody may be labeled with a fluorescent substance (e.g, fluorescamine, rhodamine, Texas Red, dansyl, or a derivative thereof), a chemiluminescent substance, or an enzyme, for example.

Moreover, a protein to be used for antibody preparation can be obtained by, based on the gene sequence information from the Genbank database, DNA cloning, construction of each plasmid, transfection to a host, culturing the transformant, and collecting the protein from the culture product. These procedures can be performed according to methods known by persons skilled in the art or methods described in documents (Molecular Cloning, T. Maniatis et al., CSH Laboratory (1983), DNA Cloning, DM. Glover, IRL PRESS (1985)), for example. Specifically, such a protein can be obtained by preparing recombinant DNA (expression vector) that enables gene expression in desired host cells, introducing the DNA into host cells for transformation, culturing the transformant, and then collecting the target protein from the thus obtained culture product.

Furthermore, in the present invention, method for screening iPS cells exhibiting no differentiation resistance may also be performed by measuring DNA-methylated state of LTR region or neighborhood thereof located in the candidate gene bodies including intron and exon. At this time, LTR means the repeat sequence derived from retrovirus. For example, as the LTR subfamilies such as LTR1, LTR1B, LTR5, LTR7, LTR8, LTR16A1, LTR16C, LTR26, LTR26E, MER48, and MLT2CB are known. Preferable LTR subfamily is LTR7 of human endogenous retroviruses (HERV)-H family in this invention. The LTR7 is located in 658 loci in gene bodies of the whole human genome. The sequence of LTR7 is shown in SEQ NO: 1. In this invention, the sequence of LTR7 include sequence having at least 90%, preferably at least 95%, 96%, 97%, 98%, or 99% sequence identity with the strand.

Examples of candidate genes are a marker of group B listed in Table 2. A preferable example of such gene is selected from the group of C4orf51, HHLA1 and, ABHD12B. Examples of LTR region in C4orf51, HHLA1, and ABHD12B is shown in SEQ NO: 2, 3, 4, 5, 6 and 7.

Example of the method of measuring DNA-methylated state involves hydrolyzing unmethylated cytosine using bisulfite. Concretely, the methods include a method that involves performing bisulfite treatment, PCR, and then sequencing, a method that involves using methylation-specific oligonucleotide (MSO) microarrays, or methylation-specific PCR that involves causing PCR primers to recognize a difference between a sequence before bisulfite treatment and the sequence after bisulfite treatment and then determining the presence or the absence of methylated DNA based on the presence or the absence of PCR products. In addition to these methods, by chromosome immunoprecipitation using a DNA methylation-specific antibody, DNA-methylated regions can be detected from specific regions by extracting DNA sequences within DNA-methylated regions, performing PCR, and then performing sequencing.

Upon screening iPS cells exhibiting no differentiation resistance, subject iPS cells in which the DNA-methylated state in the above LTR region located in the candidate gene bodies is in a DNA-methylated state can be selected as iPS cells exhibiting no differentiation resistance. Here, the expression, "the DNA-methylated state" refers to, for example, a state in which the detected methylated CpGs in the subject region account for 50%, 60%, 70%, 80%, 90% or more, preferably 100% of all detected CpGs.

As an example of a method for detecting the percentage of methylated CpGs in one arbitrarily selected cell are sequenced. Hence, the percentage can be calculated by repeatedly sequencing a template to which a PCR product has been cloned a plurality of times such as 2 or more times, preferably 5 or more times, and more preferably 10 or more times and then comparing the number of sequenced clones with the number of clones for which DNA methylation has been detected. When a pyrosequencing method is employed, the percentage can also be directly determined by measuring amount of cytosine or thymine (the amount of cytosine means amount of methylated DNAs and the amount of thymine means amount of unmethylated DNAs).

Upon screening for iPS cells exhibiting no differentiation resistance with the use of the above markers, iPS cells to be subjected to screening may be prepared by introducing a specific reprogramming factor in the form of DNA or protein into somatic cells, according to a previously established method.

A reprogramming factor may be composed of a gene that is specifically expressed in ES cells, a gene product thereof, or non-coding RNA, a gene playing an important role in maintaining undifferentiation of ES cells, a gene product thereof, or non-coding RNA, or a low-molecular-weight compound. Examples of a gene(s) encompassed by a reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used independently or in combination.

Examples of combinations of reprogramming factors include the combinations as described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, and WO2010/147612, as described in Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci U.S.A. 106: 8912-8917, Kim J B, et al. (2009), Nature. 461: 649-643, Ichida J K, et al. (2009), Cell Stem Cell. 5: 491-503, Heng J C, et al. (2010), Cell Stem Cell. 6: 167-74, Han J, et al. (2010), Nature. 463: 1096-100, Mali P, et al. (2010), Stem Cells. 28: 713-720, Maekawa M, et al. (2011), Nature. 474: 225-9.

Examples of the above reprogramming factor also include factors to be used for improving the efficiency for establishment such as histone deacetylase (HDAC) inhibitors {e.g., low-molecular weight inhibitors such as valproic acid (VPA), trichostatin A, sodium butyrate, MC 1293, and M344, and nucleic acid expression inhibitors such as siRNA and shRNA against HDAC (e.g., HDAC1 siRNA Smartpool™ (Millipore) and HuSH 29mer shRNA Constructs against HDAC1 (OriGene))}, MEK inhibitors (e.g., PD184352, PD98059, U0126, SL327, and PD0325901), Glycogen synthase kinase-3 inhibitors (e.g., Bio and CHIR99021), DNA methyl transferase inhibitors (e.g., 5-azacytidine), histone methyltransferase inhibitors (e.g., low-molecular-weight inhibitors such as BIX-01294, and nucleic acid expression inhibitors such as siRNA and shRNA against Suv39h1, Suv39h2, SetDB1, and G9a), L-channel calcium agonists (e.g., Bayk8644), butyric acid, TGF beta inhibitors or ALK5 inhibitors (e.g., LY364947, SB431542, 616453, and A-83-01), p53 inhibitors (e.g., siRNA and shRNA against p53), ARID3A inhibitors (e.g., siRNA and shRNA against ARID3A), miRNA (e.g., miR-291-3p, miR-294, miR-295, and mir-302), Wnt Signaling (e.g., soluble Wnt3a), neuropeptide Y, prostaglandins (e.g., prostaglandin E2 and prostaglandin J2), hTERT, SV40LT, UTF1, IRX6, GLIS1, PITX2, and DMRTB1. In the Description, these factors to be used for improving the efficiency for establishment are not particularly distinguished from reprogramming factors.

When a reprogramming factor is in the form of protein, it may be introduced into somatic cells by techniques such as lipofection, fusion with a cell membrane-permeable peptide (e.g., HIV-derived TAT and polyarginine), or microinjection.

Meanwhile, when a reprogramming factor is in the form of DNA, it can be introduced into somatic cells with a technique using a vector such as a virus, a plasmid, or an artificial chromosome, lipofection (or liposome transfection), or microinjection, for example. Examples of viral vectors include a retrovirus vector, a lentivirus vector (Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a Sendai virus vector (WO 2010/008054). Furthermore, examples of artificial chromosome vectors include a human artificial chromosome (HAC), a yeast artificial chromosome (YAC), and a bacterial artificial chromosome (BAC or PAC), As a plasmid, a plasmid for mammalian cells can be used (Science, 322: 949-953, 2008). A vector to be used herein can contain regulatory sequences such as a promoter, an enhancer, a ribosome binding sequence, a terminator, and a polyadenylation site so that a nuclear reprogramming substance can be expressed. Furthermore, if necessary, such a vector can further contain a selection marker sequence such as a drug resistance gene (e.g., a kanamycin resistance gene, an ampicillin resistance gene, and a puromycin resistance gene), a thymidine kinase gene, and a diphtheria toxin gene, and a reporter gene sequence such as a green fluorescent protein (GFP), beta glucuronidase (GUS), and FLAG. Moreover, the above vector can further contain LoxP sequences at the 5'-end and 3'-end of a gene encoding a reprogramming factor or a gene encoding a reprogramming factor linked to a promoter, which allows it to cleave the gene after introduction into somatic cells.

Furthermore, when a reprogramming factor is in the form of RNA, it may be introduced into somatic cells with techniques such as lipofection or microinjection. To suppress degradation, RNA with 5-methylcytidine and pseudouridine (TriLink Biotechnologies) incorporated therein may also be used (Warren L, (2010) Cell Stem Cell, 7: 618-630).

Examples of culture solutions for inducing iPS cells include 10% to 15% FBS-containing DMEM, DMEM/F12, or DME culture solutions (these culture solutions may further appropriately contain LIF, penicillin/streptomycin, puromycin, L-glutamine, nonessential amino acids, beta-mercaptoethanol, or the like) or commercially available culture solutions {e.g., a culture solution for culturing mouse ES cells (TX-WES culture solution, Thromb-X), a culture solution for culturing primate ES cells (a culture solution for primate ES/iPS cells, ReproCELL), and serum free medium (mTeSR, Stemcell Technology)}.

An example of culture methods is as follows. Somatic cells are brought into contact with a reprogramming factor on a DMEM or DMEM/F12 culture solution containing 10% FBS at 37 degrees C. in the presence of 5% CO2 and are cultured for about 4 to 7 days. Subsequently, the cells are reseeded on feeder cells (e.g., mitomycin C-treated STO cells or SNL cells). About 10 days after contact between somatic cells and the reprogramming factor, cells are cultured in a culture solution for primate ES cell culture containing bFGF. About 30 to 45 days or more after the contact, iPS cell-like colonies can be formed.

Alternatively, cells may be cultured at 37 degrees C. in the presence of 5% CO2 using a DMEM culture solution containing 10% FBS (which may further appropriately contain LIF, penicillin/streptomycin, puromycin, L-glutamine, nonessential amino acids, beta-mercaptoethanol, and the like) on feeder cells (e.g., mitomycin C-treated STO cells or SNL cells). After about 25 to 30 days or more, ES-like colonies can be formed. Examples of desirable methods include a method that involves using directly, instead of feeder cells, somatic cells to be reprogrammed (Takahashi K, et al., (2009), PLoS One, 4: e8067 or WO2010/137746) or an extracellular matrix (e.g., Laminin-5 (WO2009/123349) and matrigel (BD)).

Another example in addition to these examples is a culture method that involves culturing with serum-free medium (Sun N, et al., (2009), Proc Natl Acad Sci U.S.A., 106: 15720-15725). Furthermore, iPS cells may also be established under hypoxia conditions (0.1% or more, 15% or less oxygen concentration) in order to increase the efficiency for establishment (Yoshida Y, et al., (2009), Cell Stem Cell, 5: 237-241 or WO2010/013845).

During the above culture, a culture solution is exchanged with a fresh culture solution once a day from day 2 after the start of culture. In addition, the number of somatic cells to be used for nuclear reprogramming is not limited, but ranges from approximately $5 \times 10^3$ cells to approximately $5 \times 10^6$ cells per culture dish (100 cm2).

iPS cells can be selected depending on the shapes of the thus formed colonies. Meanwhile, when a drug resistance gene to be expressed in conjunction with a gene that is expressed when somatic cells are reprogrammed (e.g., Oct3/4 or Nanog) is introduced as a marker gene, cells are cultured in a culture solution (selection culture solution) containing a suitable medical agent, so that the thus established iPS cells can be selected. Furthermore, iPS cells can be selected through observation with a fluorescence microscope when a marker gene is a fluorescent protein gene, through addition of a luminescent substrate when a marker gene is a luminescent enzyme gene, or through addition of a chromogenic substrate when a marker gene is a chromogenic enzyme gene.

The term "somatic cells" as used herein may refer to all animal cells (preferably, mammalian cells including human cells) excluding germ-line cells (e.g., ova, oocytes, and ES cells) or totipotent cells. Examples of somatic cells include, but are not limited to, any fetal somatic cells, neonate somatic cells, and mature healthy or pathogenic somatic cells, or, any primary cultured cells, passaged cells, and established cell lines. Specific examples of somatic cells include (1) tissue stem cells (somatic stem cells) such as neural stem cells, hematopoietic stem cells, mesenchymal stem cells, and dental pulp stem cells, (2) tissue precursor cells, (3) differentiated cells such as lymphocytes, epithelial cells, endothelial cells, muscle cells, fibroblasts (e.g., skin cells), hair cells, hepatocytes, gastric mucosal cells, enterocytes, spleen cells, pancreatic cells (e.g., pancreatic exocrine cells), brain cells, pneumocytes, renal cells, and fat cells.

2. Reagent and Kit for Screening Human Induced Pluripotent Stem Cell Line

The present invention further provides a reagent for screening for a human induced pluripotent stem cell line. The reagent for screening of the present invention contains at least one type of probe, primer, or antibody for recognition of the above-described marker. Such a reagent can be used for producing a kit in combination with other reagents or apparatuses. The kit of the present invention may contain a reagent for RNA extraction, a reagent for gene extraction, a reagent for chromosome extraction, or the like. Also, the kit of the present invention may contain a means for discrimination analysis for discrimination between a cell line exhibiting differentiation resistance and a cell line exhibiting no differentiation resistance, such as documents or instructions containing procedures for discrimination analysis, a program for implementing the procedures for discrimination analysis by a computer, the program list, a recording medium containing the program recorded therein, which is readable by the computer (e.g., flexible disk, optical disk, CD-ROM, CD-R, and CD-RW), and an apparatus or a system (e.g., computer) for implementation of discrimination analysis.

EXAMPLES

The present invention will next be described in detail by way of Examples, which should not be construed as limiting the scope of the present invention.

Example 1

1. Cell

As human ES cells, KhES1, KhES3 (Suemori H, et al., Biochem Biophys Res Commun. 345: 926-32, 2006) and H9 (Thomson, J. A., et al., Science 282: 1145-1147, 1998) were used.

As human iPS cells, 9 families and 39 clones prepared by the following method were used.

(i) Six (6) factors (OCT3/4, SOX2, KLF4, L-Myc, LIN28, and p53shRNA) were introduced into CD34 positive cells (WO2010/131747) extracted from umbilical cord blood using an episomal vector (Okita K, et al., Nat Methods, 8: 409-12, 2011), so that four CB-EP6F clones were prepared.

(ii) Four (4) factors (OCT3/4, SOX2, KLF4, and c-MYC) were introduced into CD34 positive cells extracted from umbilical cord blood using a retrovirus, so that three CB-RV4F clones were prepared (WO2010/131747).

(iii) Four (4) factors (OCT3/4, SOX2, KLF4, and c-MYC) were introduced into CD34 positive cells (WO2010/131747) extracted from umbilical cord blood using the Sendai virus (Seki T, et al., Cell Stem Cell, 7: 11-4, 2010), so that five CB-SV4F clones were prepared.

(iv) Six (6) factors (OCT3/4, SOX2, KLF4, L-Myc, LIN28, and p53shRNA) were introduced into dental pulp stem cells using an episomal vector, so that two DP-EP6F clones were prepared (Okita K, et al., Nat Methods, 8: 409-12, 2011).

(v) Six (6) factors (OCT3/4, SOX2, KLF4, L-Myc, LIN28, and p53shRNA) were introduced into fibroblasts using an episomal vector, so that three FB-EP6F clones were prepared (Okita K, et al., Nat Methods, 8: 409-12, 2011).

(vi) Three (3) factors (OCT3/4, SOX2, and KLF4) were introduced into fibroblasts using retrovirus, so that four FB-RV3F clones were prepared (Okita K, et al., Nat Methods, 8: 409-12, 2011).

(vii) Four (4) factors (OCT3/4, SOX2, KLF4, and c-MYC) were introduced into fibroblasts using retrovirus, so that eleven FB-RV4F clones were prepared (Okita K, et al., Nat Methods, 8: 409-12, 2011).

(viii) Six (6) factors (OCT3/4, SOX2, KLF4, L-Myc, LIN28, and p53shRNA) were introduced into T cells (Seki T, et al., Cell Stem Cell, 7: 11-4, 2010) included in peripheral blood mononuclear cells (PBMC) using an episomal vector, so that four PM-EP6F clones were prepared (Okita K, et al., Nat Methods, 8: 409-12, 2011).

(ix) Four (4) factors (OCT3/4, SOX2, KLF4, and c-MYC) were introduced into T cells included in peripheral blood mononuclear cells (PBMC) using Sendai virus, so that four PM-SV4F clones were prepared (Seki T, et al., Cell Stem Cell, 7: 11-4, 2010).

2. Confirmation of Differentiation Resistance

To confirm differentiation resistance of ES cells and iPS cells, the aforementioned cells were subjected to differentiation induction to result in neural cells using a modified SFEBq method comprising the following steps.

(1) 10 micromolar Y27632 (WAKO) was added to a culture solution of ES cells or iPS cells and then the solution was left to stand for 3 hours.

(2) Feeder cells were removed using a CTK solution (collagenase-trypsine-KSR), the resultant was treated with Accumax (Innovate cell technologies) and then disintegrated into single cells, and the resulting cells were plated on a 96-well plate (Lipidure-coat U96w, NOF Corporation) at 9,000 cells/150 microliter/well.

(3) Cells were cultured in DMEM/F12 (Invitrogen) containing 10 micromolar Y-27632, 2 micromolar Dorsomorphin (Sigma), 10 micromolar SB431542 (Sigma), 5% KSR (Invitrogen), MEM-Non essential amino acid solution (Invitrogen), L-glutamine (Invitrogen), and 2-Mercaptoethanol (Invitrogen). One-half the medium was exchanged every 3 or 4 days with medium lacking Y-27632, Dorsomorphin, and SB431542, followed by 14 days of culture. Subsequently, the thus obtained neural cells were isolated, fixed in 37% formalin, stained with Alexa Fluor 488 Mouse anti-Oct3/4 (BD Pharmingen), and then analyzed using a flow cytometer. In the cases of CB-RV4F-2, DP-EP6F-1, FB-RV3F-3, FB-RV3F-4, FB-RV4F-5, and FB-RV4F-11, Oct3/4 positive cells were contained at 5% or higher even after differentiation induction. These iPS cells were used as the cells of cell lines exhibiting differentiation resistance. The results are shown in Table 3.

TABLE 3

Content of Oct3/4 positive cells in each iPS cell line

| patent cell name | Souce | Factor | method | Oct3/4 positive cells (%) | | | | | | | | | Max rate | determination |
|---|---|---|---|---|---|---|---|---|---|---|---|---|---|---|
| | | | | 1st | 2nd | 3rd | 4th | 5th | 6th | 7th | 8th | 9th | | |
| KhES1 | | | | 0 | 0.8 | 0.08 | 0.13 | 0.07 | 0.01 | 1.7 | 0.59 | 0 | 1.7 | |
| KhES3 | | | | 0.2 | | | | | | | | | 0.2 | ○ |
| H1 | | | | 0.13 | 0.09 | | | | | | | | 0.13 | ○ |
| H9 | | | | 0 | 0.05 | 0.1 | 0.05 | 0 | 0.3 | | | | 0.3 | ○ |
| CB-EP6F-1 | CB | OSKUL + shp53 | Episomal plasmid | 0.3 | 0.01 | | | | | | | | 0.3 | ○ |
| CB-EP6F-2 | CB | OSKUL + shp53 | Episomal plasmid | 0.3 | 0.07 | | | | | | | | 0.3 | ○ |
| CB-EP6F-3 | CB | OSKUL + shp53 | Episomal plasmid | 0.1 | 0.03 | | | | | | | | 0.1 | ○ |
| CB-EP6F-4 | CB | OSKUL + shp53 | Episomal plasmid | 4.7 | 0.1 | | | | | | | | 4.7 | |
| CB-RV4F-1 | CB | OSKM | Retro virus | 0 | 0.35 | 0.49 | | | | | | | 0.49 | ○ |
| CB-RV4F-2 | CB | OSKM | Retro virus | 10.74 | 8.69 | 19.01 | 9.6 | 14.44 | 12.78 | | | | 19.01 | x |
| CB-RV4F-3 | CB | OSKM | Retro virus | 0 | 0.39 | 0.04 | | | | | | | 0.39 | ○ |
| CB-SV4F-1 | CB | OSKM | Sendai virus | 0.9 | 0.7 | 0.7 | | | | | | | 0.9 | ○ |
| CB-SV4F-2 | CB | OSKM | Sendai virus | 0 | 0.1 | 0.1 | | | | | | | 0.1 | ○ |
| CB-SV4F-3 | CB | OSKM | Sendai virus | 0.3 | 0.1 | | | | | | | | 0.3 | ○ |
| CB-SV4F-4 | CB | OSKM | Sendai virus | 0.2 | 0.3 | | | | | | | | 0.3 | ○ |
| CB-SV4F-5 | CB | OSKM | Sendai virus | 0.1 | 0 | | | | | | | | 0.1 | ○ |
| DP-EP6F-1 | dental pulp | OSKUL + shp53 | Episomal plasmid | 13.61 | 13.91 | 2.42 | 6.1 | 2.18 | 1.3 | 1.96 | | | 13.91 | x |
| DP-EP6F-2 | dental pulp | OSKUL + shp53 | Episomal plasmid | 0.01 | 0.06 | 0.08 | | | | | | | 0.08 | ○ |
| FB-EP6F-1 | Fibro | OSKUL + shp53 | Episomal plasmid | 0 | 0.02 | | | | | | | | 0.02 | ○ |
| FB-EP6F-2 | Fibro | OSKUL + shp53 | Episomal plasmid | 0.16 | 0.02 | | | | | | | | 0.16 | ○ |
| FB-EP6F-3 | Fibro | OSKUL + shp53 | Episomal plasmid | 0.11 | 0.05 | 0.1 | | | | | | | 0.11 | ○ |
| FB-RV3F-1 | Fibro | OSK | Retro virus | 0 | 0 | 0.1 | | | | | | | 0.1 | ○ |
| FB-RV3F-2 | Fibro | OSK | Retro virus | 0.28 | 0.1 | | | | | | | | 0.28 | ○ |
| FB-RV3F-3 | Fibro | OSK | Retro virus | 0 | 7.64 | 14.25 | 1.19 | | | | | | 14.25 | x |
| FB-RV3F-4 | Fibro | OSK(M) | Retro virus | 1.24 | 12.41 | 8.4 | 8.9 | 14.9 | 14.16 | 4 | | | 14.9 | x |
| FB-RV4F-1 | Fibro | OSKM | Retro virus | 0.05 | 0.4 | | | | | | | | 0.4 | ○ |
| FB-RV4F-2 | Fibro | OSKM | Retro virus | 0.15 | 0.26 | 0 | 0 | 0 | 0.01 | 0.04 | | | 0.26 | ○ |
| FB-RV4F-3 | Fibro | OSKM | Retro virus | 0.92 | 3.62 | 11.2 | | | | | | | 11.2 | x |
| FB-RV4F-4 | Fibro | OSKM | Retro virus | 0.04 | 0.04 | | | | | | | | 0.04 | ○ |
| FB-RV4F-5 | Fibro | OSKM | Retro virus | 17.47 | 5.19 | 12.6 | 8.3 | 6.94 | 17.1 | | | | 17.47 | x |
| FB-RV4F-6 | Fibro | OSKM | Retro virus | 0 | 3.64 | | | | | | | | 3.64 | |
| FB-RV4F-7 | Fibro | OSKM | Retro virus | 0.01 | 0.07 | | | | | | | | 0.07 | ○ |
| FB-RV4F-8 | Fibro | OSKM | Retro virus | 0 | 0.09 | | | | | | | | 0.09 | ○ |
| FB-RV4F-9 | Fibro | OSKM | Retro virus | 0 | 0.05 | | | | | | | | 0.05 | ○ |
| FB-RV4F-10 | Fibro | OSKM | Retro virus | 0.03 | 0.02 | | | | | | | | 0.03 | ○ |
| FB-RV4F-11 | Fibro | OSKM | Retro virus | 1.11 | 13.06 | 14.39 | | | | | | | 14.39 | x |
| PB-EP6F-1 | PBMN | OSKUL + shp53 | Episomal plasmid | 0.1 | 0.04 | 0.13 | | | | | | | 0.13 | ○ |
| PB-EP6F-2 | PBMN | OSKUL + shp53 | Episomal plasmid | 4.7 | 0.02 | | | | | | | | 4.7 | |

TABLE 3-continued

Content of Oct3/4 positive cells in each iPS cell line

| patent cell name | Source | Factor | method | 1st | 2nd | 3rd | 4th | 5th | 6th | 7th | 8th | 9th | Max rate | determination |
|---|---|---|---|---|---|---|---|---|---|---|---|---|---|---|
| PB-EP6F-3 | PBMN | OSKUL + shp53 | Episomal plasmid | 0.2 | 0.02 | | | | | | | | 0.2 | ○ |
| PB-EP6F-4 | PBMN | OSKUL + shp53 | Episomal plasmid | 0.1 | 0.94 | | | | | | | | 0.94 | ○ |
| PB-SEP4F-1 | PBMN | OSKM | Sendai virus | 0.1 | 0.1 | | | | | | | | 0.1 | ○ |
| PB-SV4F-2 | PBMN | OSKM | Sendai virus | 0.1 | 0.2 | | | | | | | | 0.2 | ○ |
| PB-SV4F-3 | PBMN | OSKM | Sendai virus | 0.1 | 1.3 | 1.3 | | | | | | | 1.3 | ○ |
| PB-SV4F-4 | PBMN | OSKM | Sendai virus | 0.1 | 0.2 | 0.4 | | | | | | | 0.4 | ○ |

"○" means the clone exhibiting no differentiation resistance.
"x" measns the clone exhibiting differentiation resistance.

3. Identification of Differentiation Resistance Marker

RNA was collected from 5 iPS cell lines exhibiting differentiation resistance (CB-RV4F-2, DP-EP6F-1, FB-RV3F-3, FB-RV3F-4, and FB-RV4F-5) and 27 iPS cell lines (including ES cells) exhibiting no differentiation resistance. RNA expression was measured using microarrays (Human GE G3 8x60k, Agilent). Table 4 shows marker groups that were expressed in cell lines exhibiting no differentiation resistance at a level 5 or more times higher than that in cell lines exhibiting differentiation resistance. Similarly, Table 5 shows marker groups that were expressed in cell lines exhibiting no differentiation resistance at a level 5 or more times lower than that in cell lines exhibiting differentiation resistance. Here, four markers, the P value of each of which obtained by t-test was 0.05 or less, were confirmed from Table 4 (DLX5, MEIS2, lincRNA:chr17:21434064-21435857 reverse strand, GREB1L) and 12 markers, the P value of each of which obtained by t-test was 0.05 or less, were confirmed from Table 5 (C4orf51, C7orf57, lincRNA:chr7:124873114-124899839 reverse strand, OC90, lincRNA:chr8:133071643-133092468 reverse strand, lincRNA:chr8:133076031-133093351 reverse strand, ABHD12B, lincRNA:chr18:54721302-54731677 reverse strand, ZNF541, TBX1, CXorf61, DB090170 TESTI4 *Homo sapiens* cDNA clone TESTI4038997 5', mRNA sequence [DB090170]).

TABLE 4

Markers for cell lines exhibiting no differentiation resistance

| Marker name | Genbank Accession | Chromosome Number | Strand Direction | Region | P < 0.05 |
|---|---|---|---|---|---|
| lincRNA:chr1:852245-854050 reverse strand | | chr1 | − | 852,245-854,050 | |
| GPR177 | NM_001002292 | chr1 | − | 29,518,977-29,543,121 | |
| VTCN1 | NM_024626 | chr1 | − | 117,686,209-117,753,549 | |
| lincRNA:chr1:142803013-142804254 reverse strand | | chr1 | − | 142,803,013-142,804,254 | |
| APOA2 | NM_001643 | chr1 | − | 161,192,083-161,193,418 | |
| WNT6 | NM_006522 | chr2 | + | 23,961,932-23,965,019 | |
| EPAS1 | NM_001430 | chr2 | + | 46,524,541-46,613,842 | |
| COL3A1 | NM_000090 | chr2 | + | 189,839,099-189,877,472 | |
| SLC40A1 | NM_014585 | chr2 | − | 190,425,316-190,445,537 | |
| S100P | NM_005980 | chr4 | + | 6,695,566-6,698,897 | |
| HOPX | NM_139211 | chr4 | − | 57,514,154-57,547,872 | |
| GUCY1A3 | NM_000856 | chr4 | + | 156,587,862-156,658,214 | |
| CDH10 | NM_006727 | chr5 | − | 24,487,209-24,645,085 | |
| HAPLN1 | NM_001884 | chr5 | − | 82,934,017-83,016,896 | |
| PITX1 | NM_002653 | chr5 | − | 134,363,424-134,369,964 | |
| HAND1 | NM_004821 | chr5 | − | 153,854,532-153,857,824 | |
| CGA | NM_000735 | chr6 | − | 87,795,222-87,804,824 | |
| AQP1 | NM_198098 | chr7 | + | 30,951,415-30,965,131 | |
| DLX6 | NM_005222 | chr7 | + | 96,635,290-96,640,352 | |
| DLX5 | NM_005221 | chr7 | − | 96,649,702-96,654,143 | ○ |
| SOX17 | NM_022454 | chr8 | + | 55,370,495-55,373,456 | |
| FLJ45983 | NR_024256 | chr10 | − | 8,092,413-8,095,447 | |
| PLCE1 | NM_016341 | chr10 | + | 95,753,746-96,088,149 | |
| H19 | NR_002196 | chr11 | − | 2,016,406-2,019,065 | |
| lincRNA:chr11:2016408-2017024 reverse strand | | chr11 | − | 2,016,408-2,017,024 | |
| lincRNA:chr11:2017517-2017651 forward strand | | chr11 | + | 2,017,517-2,017,651 | |
| IGF2 | NM_000612 | chr11 | − | 2,150,350-2,182,439 | |
| P2RY6 | NM_176798 | chr11 | + | 72,975,570-73,009,664 | |

TABLE 4-continued

Markers for cell lines exhibiting no differentiation resistance

| Marker name | Genbank Accession | Chromosome Number | Strand Direction | Region | P < 0.05 |
|---|---|---|---|---|---|
| SLN | NM_003063 | chr11 | − | 107,578,101-107,582,787 | |
| NNMT | NM_006169 | chr11 | + | 114,166,535-114,183,238 | |
| APOA1 | NM_000039 | chr11 | − | 116,706,459-116,708,338 | |
| ERP27 | NM_152321 | chr12 | − | 15,066,976-15,091,463 | |
| LUM | NM_002345 | chr12 | − | 91,497,232-91,505,542 | |
| CCDC92 | NM_025140 | chr12 | − | 124,420,955-124,457,163 | |
| CDX2 | NM_001265 | chr13 | − | 28,536,278-28,543,317 | |
| FLJ41170 | AK021542 | chr14 | + | 81,527,645-81,529,369 | |
| MEG3 | NR_003530 | chr14 | + | 101,292,445-101,327,363 | |
| lincRNA:chr14:101292469-101299626 forward strand | | chr14 | + | 101,292,469-101,299,626 | |
| lincRNA:chr14:101295637-101302637 forward strand | | chr14 | + | 101,295,637-101,302,637 | |
| lincRNA:chr14:101296681-101298460 forward strand | | chr14 | + | 101,296,681-101,298,460 | |
| lincRNA:chr14:101298129-101300147 forward strand | | chr14 | + | 101,298,129-101,300,147 | |
| lincRNA:chr14:101324825-101327247 forward strand | | chr14 | + | 101,324,825-101,327,247 | |
| MEG8 | NR_024149 | chr14 | + | 101,361,107-101,373,305 | |
| lincRNA:chr14:101365673-101366049 forward strand | | chr14 | + | 101,365,673-101,366,049 | |
| lincRNA:chr14:101396955-101397357 forward strand | | chr14 | + | 101,396,955-101,397,357 | |
| lincRNA:chr14:101430757-101433381 forward strand | | chr14 | + | 101,430,757-101,433,381 | |
| lincRNA:chr14:101434059-101436282 forward strand | | chr14 | + | 101,434,059-101,436,282 | |
| lincRNA:chr14:101472355-101473369 forward strand | | chr14 | + | 101,472,355-101,473,369 | |
| DIO3 | NM_001362 | chr14 | + | 102,027,688-102,029,789 | |
| MEIS2 | NM_170677 | chr15 | − | 37,183,232-37,393,500 | ○ |
| PRTG | NM_173814 | chr15 | − | 55,903,738-56,035,177 | |
| C17orf51 | NM_001113434 | chr17 | − | 21,431,571-21,454,941 | |
| lincRNA:chr17:21434064-21435857 reverse strand | | chr17 | − | 21,434,064-21,435,857 | ○ |
| lincRNA:chr17:21435180-21454915 reverse strand | | chr17 | − | 21,435,180-21,454,915 | |
| lincRNA:chr17:21435959-21436405 reverse strand | | chr17 | − | 21,435,959-21,436,405 | |
| CCR7 | NM_001838 | chr17 | − | 38,710,021-38,721,736 | |
| KRT23 | NM_015515 | chr17 | − | 39,078,952-39,093,836 | |
| GREB1L | NM_001142966 | chr18 | + | 18,822,203-19,102,791 | ○ |
| GATA6 | NM_005257 | chr18 | + | 19,749,416-19,782,227 | |
| TTR | NM_000371 | chr18 | + | 29,171,730-29,178,987 | |
| UCA1 | NR_015379 | chr19 | + | 15,939,757-15,946,230 | |
| FLRT3 | NM_198391 | chr20 | − | 14,304,639-14,318,313 | |
| lincRNA:chrX:73040495-73047819 reverse strand | | chrX | − | 73,040,495-73,047,819 | |
| VGLL1 | NM_016267 | chrX | + | 135,614,311-135,638,966 | |
| RPS4Y1 | NM_001008 | chrY | + | 2,709,623-2,734,997 | |
| DDX3Y | NM_001122665 | chrY | + | 15,016,019-15,032,390 | |
| RPS4Y2 | NM_001039567 | chrY | + | 22,917,954-22,942,918 | |

TABLE 5

Markers for cell lines exhibiting differentiation resistance

| Marker name | Genbank Accession | Chromosome Number | Strand Direction | Region | P < 0.05 |
|---|---|---|---|---|---|
| DMRTB1 | NM_033067 | chr1 | + | 53,925,072-53,933,158 | |
| lincRNA:chr1:73430887-73446112 reverse strand | | chr1 | − | 73,430,887-73,446,112 | |
| lincRNA:chr1:73444697-73444997 reverse strand | | chr1 | − | 73,444,697-73,444,997 | |
| C4orf51 | NM_001080531 | chr4 | + | 146,601,356-146,653,949 | ○ |
| PCDHA1 | NM_031410 | chr5 | + | 140,165,876-140,391,929 | |
| lincRNA:chr6:95250854-95263604 reverse strand | | chr6 | − | 95,250,854-95,263,604 | |

TABLE 5-continued

Markers for cell lines exhibiting differentiation resistance

| Marker name | Genbank Accession | Chromosome Number | Strand Direction | Region | P < 0.05 |
|---|---|---|---|---|---|
| lincRNA:chr6:14280358-14285376 reverse strand | | chr6 | − | 14,280,358-14,285,376 | |
| lincRNA:chr6:14283301-14285685 reverse strand | | chr6 | − | 14,283,301-14,285,685 | |
| C7orf57 | NM_001100159 | chr7 | + | 48,075,117-48,100,894 | ○ |
| lincRNA:chr7:124873114-124899839 reverse strand | | chr7 | − | 124,873,114-124,899,839 | ○ |
| lincRNA:chr8:129599518-129624118 reverse strand | | chr8 | − | 129,599,518-129,624,118 | |
| OC90 | NM_001080399 | chr8 | − | 133,036,467-133,071,627 | ○ |
| lincRNA:chr8:133071643-133092468 reverse strand | | chr8 | − | 133,071,643-133,092,468 | ○ |
| lincRNA:chr8:133073732-133075753 reverse strand | | chr8 | − | 133,073,732-133,075,753 | |
| HHLA1 | NM_001145095 | chr8 | − | 133,073,733-133,117,512 | |
| lincRNA:chr8:133076031-133093351 reverse strand | | chr8 | − | 133,076,031-133,093,351 | ○ |
| lincRNA:chr8:138387843-138421643 reverse strand | | chr8 | − | 138,387,843-138,421,643 | |
| lincRNA:chr8:138418343-138425831 reverse strand | | chr8 | − | 138,418,343-138,425,831 | |
| NDUFA4L2 | NM_020142 | chr12 | − | 57,628,686-57,634,545 | |
| lincRNA:chr13:54698462-54707001 reverse strand | | chr13 | − | 54,698,462-54,707,001 | |
| ABHD12B | NM_181533 | chr14 | + | 51,338,878-51,371,688 | ○ |
| lincRNA:chr18:54721302-54731677 reverse strand | | chr18 | − | 54,721,302-54,731,677 | ○ |
| ZNF208 | NM_007153 | chr19 | − | 22,148,897-22,193,745 | |
| ZNF257 | NM_033468 | chr19 | + | 22,235,266-22,273,905 | |
| ZNF676 | NM_001004111 | chr19 | − | 22,361,903-22,379,753 | |
| ZNF541 | NM_001101419 | chr19 | − | 48,023,947-48,059,113 | ○ |
| TBX1 | NM_080647 | chr22 | + | 19,744,226-19,771,116 | ○ |
| CXorf61 | NM_001017978 | chrX | − | 115,592,852-115,594,137 | ○ |
| DB090170 TESTI4 Homo sapiens cDNA clone TESTI4038997 5′, mRNA sequence [DB090170] | DB090170 | chrX | − | | ○ |

Example 2

(1) Cell

The above four iPS cell lines exhibiting differentiation resistance (CB-RV4F-2, DP-EP6F-1, FB-RV3F-4, and FB-RV4F-5) were seeded and then the thus obtained colonies were picked up, so that 15 subclones were obtained from CB-RV4F-2, 15 subclones were obtained from DP-EP6F-1, 10 subclones were obtained from FB-RV3F-4, and 11 subclones were obtained from FB-RV4F-5.

(2) Confirmation of Differentiation Resistance

To confirm the differentiation resistance of ES cells and iPS cells, differentiation induction to neural cells was performed using the above modified SFEBq method, and then the contents of TRA-1-60 positive cells were examined using a flow cytometer. As a result, 12 out of 15 CB-RV4F-2 subclones contained TRA-1-60 positive cells at 1% or more after induction of cell differentiation to neural cells (Table 6). Similarly, 12 out of 15 DP-EP6F-1 subclones (Table 7), 8 out of 10 FB-RV3F-4 subclones (Table 8), and 3 out of 11 FB-RV4F-5 subclones (Table 9) contained TRA-1-60 positive cells at 1% or more. These 35 subclones found to contain TRA-1-60 positive cells at 1% or more were screened for as iPS cell lines exhibiting differentiation resistance.

TABLE 6

TRA-1-60 positive cell content in CB-RV4F-2 subclone

| | TRA-1-60 positive cells (%) | | | |
|---|---|---|---|---|
| subclone name | 1st try | 2nd try | 3rd try | Average |
| CB-RV4F-2 sub1 | 0.1 | 0.1 | 0.1 | 0.1 |
| CB-RV4F-2 sub2 | 24.6 | 10.1 | 11.5 | 15.4 |
| CB-RV4F-2 sub3 | 17.2 | 14.7 | 4.2 | 12.03333 |
| CB-RV4F-2 sub4 | 8.4 | 20 | 41.8 | 23.4 |
| CB-RV4F-2 sub5 | 12 | 13.8 | 11 | 12.26667 |
| CB-RV4F-2 sub6 | 20.7 | 15 | 14 | 16.56667 |
| CB-RV4F-2 sub7 | 25.1 | 21.8 | 24.1 | 23.66667 |
| CB-RV4F-2 sub8 | 10 | 4.6 | 2 | 5.533333 |
| CB-RV4F-2 sub9 | 9.6 | 3.5 | 1.9 | 5 |
| CB-RV4F-2 sub10 | 17.5 | 11.8 | 15.5 | 14.93333 |
| CB-RV4F-2 sub11 | 0.1 | 0.3 | 0.1 | 0.166667 |
| CB-RV4F-2 sub12 | 28.8 | 23.8 | 15.7 | 22.76667 |
| CB-RV4F-2 sub13 | 23.1 | 21.5 | 12.1 | 18.9 |
| CB-RV4F-2 sub14 | 14.2 | 7.3 | 11.8 | 11.1 |
| CB-RV4F-2 sub15 | 0 | 0.5 | 0.1 | 0.2 |
| CB-RV4F-2 | 27.3 | 26 | 8 | 20.43333 |
| H9 | 0.2 | 0.1 | 0.2 | 0.166667 |
| khES1 | 0 | 0 | 0.3 | 0.1 |
| khES3 | 0.1 | 0 | 0.1 | 0.066667 |

TABLE 7

TRA-1-60 positive cell content in DP-EP6F-1 subclone

| subclone name | TRA-1-60 positive cells (%) |
|---|---|
| DP-EP6F-1 sub1 | 8.8 |
| DP-EP6F-1 sub2 | 21 |
| DP-EP6F-1 sub3 | 48.3 |
| DP-EP6F-1 sub4 | 11.4 |
| DP-EP6F-1 sub5 | 0.6 |
| DP-EP6F-1 sub6 | 8.1 |
| DP-EP6F-1 sub7 | 43.9 |
| DP-EP6F-1 sub8 | 9.5 |
| DP-EP6F-1 sub9 | 0.2 |
| DP-EP6F-1 sub10 | 22 |
| DP-EP6F-1 sub11 | 0.1 |
| DP-EP6F-1 sub12 | 44.1 |
| DP-EP6F-1 sub13 | 41.3 |
| DP-EP6F-1 sub14 | 10.9 |
| DP-EP6F-1 sub15 | 16.9 |
| DP-EP6F-1 | 53.5 |
| H9 | 0.1 |
| khES3 | 0.1 |

TABLE 8

TRA-1-60 positive cell content in FB-RV3F-4 subclone

| | TRA-1-60 (%) | | | |
|---|---|---|---|---|
| subclone name | 1st try | 2nd try | 3rd try | Average |
| FB-RV3F-4 sub1 | 10.9 | 29.1 | 9.9 | 16.63333 |
| FB-RV3F-4 sub2 | 9.4 | 28.3 | 8.5 | 15.4 |
| FB-RV3F-4 sub3 | 7.7 | 26 | 6.7 | 13.46667 |
| FB-RV3F-4 sub4 | 0 | 0.1 | 0 | 0.033333 |
| FB-RV3F-4 sub5 | 0.1 | 0 | 0 | 0.033333 |
| FB-RV3F-4 sub6 | 6.7 | 12.9 | 7.5 | 9.033333 |
| FB-RV3F-4 sub7 | 14 | 12.5 | 6.6 | 11.03333 |
| FB-RV3F-4 sub8 | 12.9 | 25.9 | 24.8 | 21.2 |
| FB-RV3F-4 sub9 | 7.5 | 9.5 | 5.2 | 7.4 |
| FB-RV3F-4 sub10 | 21.4 | 32 | 21 | 24.8 |
| FB-RV3F-4 | 30.8 | 41.4 | 19.9 | 30.7 |
| H9 | 0.1 | 0 | 0.1 | 0.066667 |
| khES1 | 0.1 | 0.1 | 0 | 0.066667 |
| khES3 | 0 | 0.1 | 0 | 0.033333 |

TABLE 9

TRA-1-60 positive cell content in FB-RV4F-5 subclone

| | TRA-1-60 positive cells (%) | | |
|---|---|---|---|
| subclone name | 1st try | 2nd try | Average |
| FB-RV4F-5 sub1 | 0.1 | 0.8 | 0.45 |
| FB-RV4F-5 sub2 | 3.8 | 13.1 | 8.45 |
| FB-RV4F-5 sub3 | 0.3 | 0.5 | 0.4 |
| FB-RV4F-5 sub4 | 0.1 | 0.1 | 0.1 |
| FB-RV4F-5 sub5 | 14.8 | 20.9 | 17.85 |
| FB-RV4F-5 sub6 | 38.9 | 19.6 | 29.25 |
| FB-RV4F-5 sub7 | 0.1 | 0 | 0.05 |
| FB-RV4F-5 sub8 | 0.1 | 0.2 | 0.15 |
| FB-RV4F-5 sub9 | 0.4 | 0.1 | 0.25 |
| FB-RV4F-5 sub10 | 0.2 | 0.7 | 0.45 |
| FB-RV4F-5 sub11 | 0.1 | 0.8 | 0.45 |
| FB-RV4F-5 | 2.8 | 7.7 | 5.25 |
| H9 | 0.2 | 0.1 | 0.15 |
| khES1 | 0.1 | 0.3 | 0.2 |
| khES3 | 0.1 | 0.3 | 0.2 |

Identification of Differentiation Resistance Marker

RNAs were extracted from the 35 subclones exhibiting differentiation resistance and 16 subclones exhibiting no differentiation resistance, which had been screened for by the above method, and then the expression level of each RNA was examined using microarrays. As a result, lincRNA and mRNA were expressed at significantly high levels in subclones exhibiting differentiation resistance, as shown in Table 10.

TABLE 10

| Marker name | Genbank Accession | Chromosome Number | Strand Direction | Region | P < 0.05 |
|---|---|---|---|---|---|
| OC90 | NM_001080399 | chr8 | − | 133,036,467-133,071,627 | ○ |
| lincRNA:chr8:133071643-133092468 reverse strand | | chr8 | − | 133,071,643-133,092,468 | ○ |
| lincRNA:chr8:133073732-133075753 reverse strand | | chr8 | − | 133,073,732-133,075,753 | ○ |
| HHLA1 | NM_001145095 | chr8 | − | 133,073,733-133,117,512 | ○ |
| lincRNA:chr8:133076031-133093351 reverse strand | | chr8 | − | 133,076,031-133,093,351 | ○ |
| lincRNA:chr8:133090096-133097869 reverse strand | | chr8 | − | 133,090,096-133,097,869 | ○ |
| ABHD12B | NM_181533 | chr14 | + | 51,338,878-51,371,688 | ○ |

Example 3

RNA expression of C4orf51, HHLA1 and ABHD12B contained in the Table 5 (Example 1) and Table 10 (Example 2) as the markers for cell lines exhibiting differentiation resistance was measured in 6 clones exhibiting differentiation resistance and 6 clones exhibiting no differentiation resistance with quantitative PCR (FIG. 1). It was confirmed that these marker genes were expressed in the clone exhibiting differentiation resistance as the same manner of former result. Furthermore, it was known that these genes have the LTR7 region in their gene bodies (FIG. 2). Consequently, percentage of methylated cytosines in CpG dinucleotide in LTR7 region or neighborhood thereof was measured with Pyrosequencing (FIG. 3). Briefly, pyrosequencing was carried out with primers designed with the Pyromark Assay Design Software 2.0 (Qiagen). The primer sequence and the CpG dinucleotide in LTR7 region is shown in Tables 11 and 12. PCR was performed in a 25 microliter reaction mix containing 25 ng bisulfate-converted DNA, 1× Pyromark PCR Master Mix (Qiagen), 1× Coral Load Concentrate (Qiagen), and 0.3 micromolar forward and 5' biotinylated reverse primers. PCR conditions were 45 cycles of 95 degrees C. for 30 s, 50 degrees C. for 30 s, and 72 degrees C. for 30 s. PCR product was bound to streptavidin sepharose beads (Amersham Biosciences), and then was purified, washed, denatured, and washed again. Then, 0.3 micromol/L pyrosequencing primer was annealed to the purified PCR product. Pyrosequencing reactions were performed in the PSQ HS 96 Pyrosequencing System. The degree of methylation was expressed as percentage of methylated cytosines divided by the sum of methylated and unmethylated cytosines (percentage of 5 mC). To validate PCR pyrosequencing assay, each CpG dinucleotide position was assayed in triplicate and their averages were used in final analysis. As the result, the methylated status of CpG dinucleotide position in the LTR7 region or neighborhood thereof located in C4orf51, HHLA1 and ABHD12B gene bodies were significantly high level.

TABLE 11

| Region | primer | sequence | SEQ ID NO |
|---|---|---|---|
| HHLA1 3'LTR-1 (pos.1,2) | forward primer | TGTGAAAGTTTTTTTTTGGTTTATTTTG | 8 |
|  | reverse primer | CCTCTCCAAAACTCTAATACATATCTT | 9 |
|  | pyrosequencing primer | ACAATAAAACTATTTATTTCACCT | 10 |
| HHLA1 3'LTR-2 (pos.3,4) | forward primer | AAAGTTTGTTTGGTGGTTTTTT | 11 |
|  | reverse primer | AAAAAAATTAATCTCCTCCATATACCTT | 12 |
|  | pyrosequencing primer | TTGTTTGGTGGTTTTTTTA | 13 |
| ABHD12B before 5'LTR (pos.1,2,3) | forward primer | TGTGTATTAATGTATGGTTAATTTTGGTAA | 14 |
|  | reverse primer | CAAACCATCTAAACAAATACCTACAA | 15 |
|  | pyrosequencing primer | GTTGTTTTTTATGTAGTGTTT | 16 |
| ABHD12B 5'LTR (pos.4) | forward primer | TGTGTATTAATGTATGGTTAATTTTGGTAA | 14 |
|  | reverse primer | CAAACCATCTAAACAAATACCTACAA | 15 |
|  | pyrosequencing primer | TTAGGTTTTTGAGTTTAAGTTAA | 17 |
| ABHD12B 3'LTR (pos.1,2) | forward primer | AAGTTTGTTTGGTGGTTTTTTTATATAGA | 18 |
|  | reverse primer | ACCATTCCACAATCATAATAAAATACTTT | 19 |
|  | pyrosequencing primer | ACCAATAACAATAAACAAAATTT | 20 |
| ABHD12B after 3'LTR-1 (pos.3) | forward primer | GTTGTGGAGTTATTTAGATTTGGGTTTA | 21 |
|  | reverse primer | CTTTTCCTACCATACATAACACTTTAAC | 22 |
|  | pyrosequencing primer | TTTTTTATTAAGGGGTTGG | 23 |
| ABHD12B after 3'LTR-2 (pos.4) | forward primer | TTTTTTTTTTGAAGGTGAGGGAAAGTAGTT | 24 |
|  | reverse primer | AACCTATAAATCTCCATTTCTCTCATCTC | 25 |
|  | pyrosequencing primer | TGGTAGGAATGGGGT | 26 |
| C4orf51 5'LTR (pos.1,2) | forward primer | GGATAATTTGAAAATGTTTTTGGTTAAGG | 27 |
|  | reverse primer | ATAATTCTTCAATTACTTCAAACCATCTA | 28 |
|  | pyrosequencing primer | GGTTTTTGAGTTTAAGTTAAG | 29 |
| C4orf51 3'LTR (pos.1,2,3) | forward primer | TTTTTTTTTTGGTTTATTTTGGTTTAAAAG | 30 |
|  | reverse primer | ACAAACCATATCTCAAATAAAAAATTTCAT | 31 |
|  | pyrosequencing primer | ATATAAATTTGTTTGGTGG | 32 |

TABLE 12

| Region | Sequence | SEQ ID NO |
|---|---|---|
| HHLA1 3'LTR-1 | TGTGAAAGTCCTCTTCCTGGCTCATCCTGGC ATCAAAAAGCCCCCCACTGAGCACCTTGAGA CCCCCACTCCTGCCCGCCAGAGAACAAACCC CCTTTGACTGTAATTTTCCTTTACCTACCCA AATCCTATAAAACGGCCCCACCCTTATCTCC CTTCACTGACTCTCTTTT<u>CG</u>GACTCAGCC<u>CG</u> CCTGCACCCAGGTGAAATAAACAGCTTTATT GCTCACACAAAGCCTGTTTGGTGGTCTCTTC ACACGGACGCACATGAAATTTAGTTGTATCC ATAAGGCATATGGAGGAGACTAATTCCTCTT CCAAAGACATGTACCAGAGTCCTGGAGAGG | 33 |
| HHLA1 3'LTR-2 | AAAGCCTGTTTGGTGGTCTCTTCACA<u>CG</u>GA<u>C</u> <u>G</u>CACATGAAATTTAGTTGTATCCATAAGGCA TATGGAGGAGACTAATTCCTCT | 34 |
| ABHD12B before 5'LTR and 5'LTR | TGTGTACCAATGTATGGTCAATTTTGGCAAA TTTTCCATATGCTTGAAAAGAATGTGTTCTG CTGTTTTTCATGCAGTGTTCTATGTA<u>CG</u>T<u>CG</u> ATTGAAT<u>CG</u>GGATTATTAACCATGCTTAAAT TTGTCAGGCCTCTGAGCCCAAGCCAAGCCAT <u>CG</u>CATCCCCTGTGACTTGCAGGTATCTGCCC AGATGGCCTG | 35 |
| ABHD12B 3'LTR | AAGCCTGTTTGGTGGTCTCTTCACACAGA<u>CG</u> <u>CG</u>CATGAAAAAATTTTGTCTATTGTTACTGG TTTTTTGGACTGCTTGCTTTTTCAGTTACTC AAAGAGGATTATTAAAGTACCTCATCATGAT TGTGGAATGGT | 36 |
| ABHD12B after 3'LTR-1 | GCTGTGGAGCCACTCAGACTTGGGTTCAAAT CTGTCCTTGGCCACATACCCTTTGTGACCTT GGTAAATTGTTTCTCCCTAAGTTTTCCCATT TTTTTACCAAGGGGTTGG<u>CG</u>AAGACCACTGC ACAGGGTTGTTGTGAAGACTGAATTAAGTAA GATAATGTATGTAAAGTACCCAGCTGCTAGT AAGCACTAGACAAATACTTGITCCITTCCGT CCCTCTTTCTGTTACAAATTAGGCTAAAGTG TTATGTATGGCAGGAAAAG | 37 |
| ABHD12B after 3'LTR-2 | CTTCTTTCTTGAAGGTGAGGGAAAGCAGTTA GGAAACAGAGCGAGGAACAGGTGAATGTTAA CTCAGACCCCTGGCAGGAATGGGGCTGTTCT A<u>CG</u>TTATAAACTGCCTGAGAGTTAATAGAGG ACTTCCACACAAGTCTTTCGCACTCGTTATT CTTTTAAATCCTCACAGCAACTCTCTGAGTT TGTCATCATTGCTTCCACTTAGAGATGAGAG AAATGGAGACCTATAGGTT | 38 |
| C4orf51 5'LTR | GGATAATTTGAAAATGCCCTTGGCCAAGGGG AAGCTCCACCAGTCAGTTGGGGGAGCTTAGA ATTTTATTTTTGGTTTACAAGTTCATTATAT ATATTTTGGATATTAACTCCTTGTCAGGCCT CTGAGCCCAAGCCAAGCCATCGCATCCCCTG TGACTTGCACATATA<u>CG</u>CCCAGATGGCCTGA AGTAACTGAAGAATCAC | 39 |
| C4orf51 3'LTR | TCCTTTTCCTGGCTCATCCTGGCTCAAAAGC ACCCCCACTGAGCACCTTGCGACCCCCACTC CTGCCCGCCAGAGAACAAACCCCCTTTGACT GTAATTTTCCTTTACCTACCCAAATCCTATA AAACGGCCCCACCCTTAACTCCCTTCACTGA CTCTCTTTTCGGACTCAGCCCACCTGTACCC AGGTGATTAAAAGCTTTATTGCTCACACAAA ACCTGTTTGGTGGTCTCTTCACACGGA<u>CGCG</u> CATGAAACTCCTTATCTGAGATATGGTTTGC | 40 |

"Underline CG sequence" is analyzed for DNA-methylated state.

From the above result, clone exhibiting differentiation resistance can be sorted by the recognition of the expression of C4orf51, HHLA1 and ABHD12B. Similarly, clone exhibiting differentiation resistance can be sorted by the recognition of the DNA-methylated state in LTR7 region or neighborhood thereof located in C4orf51, HHLA1, and ABHD12B gene bodies.

All publications, patents, and patent applications cited herein are incorporated herein by reference in their entirety.

INDUSTRIAL APPLICABILITY

The invention of the present application can be used in the fields of producing regenerative medicine materials.

The invention claimed is:

1. A method for screening for a human induced pluripotent stem cell line exhibiting no differentiation resistance, comprising the steps of:
   (i) measuring expression of HHLA1 mRNA, and
   (ii) selecting a human induced pluripotent stem cell line in which the HHLA1 mRNA does not express, and
   wherein said selected human induced pluripotent stem cell line exhibits no differentiation resistance.

2. A method for screening for a human induced pluripotent stem cell line exhibiting no differentiation resistance, comprising the steps of;
   (i) measuring expression of HHLA1 mRNA, and
   (ii) selecting a human induced pluripotent stem cell line in which an expression level of HHLA1 mRNA is equal to the expression level of a control ES cell line or a control induced pluripotent stem cell line known to exhibit no differentiation resistance, or lower than the expression level of an induced pluripotent stem cell line known to exhibit differentiation resistance, and
   wherein said selected human induced pluripotent stem cell line exhibits no differentiation resistance.

* * * * *